(12) United States Patent
Rowland et al.

(10) Patent No.: US 12,060,403 B2
(45) Date of Patent: Aug. 13, 2024

(54) METHODS AND COMPOSITIONS FOR TREATING AND PROTECTING AGAINST PORCINE REPRODUCTIVE AND RESPIRATORY SYNDROME VIRUS

(71) Applicant: Kansas State University Research Foundation, Manhattan, KS (US)

(72) Inventors: Raymond R. R. Rowland, Manhattan, KS (US); Ana Stoian, Manhattan, KS (US)

(73) Assignee: Kansas State University Research Foundation, Manhattan, KS (US)

(*) Notice: Subject to any disclaimer, the term of this patent is extended or adjusted under 35 U.S.C. 154(b) by 635 days.

(21) Appl. No.: 16/756,756

(22) PCT Filed: Oct. 16, 2018

(86) PCT No.: PCT/US2018/056065
§ 371 (c)(1),
(2) Date: Apr. 16, 2020

(87) PCT Pub. No.: WO2019/079285
PCT Pub. Date: Apr. 25, 2019

(65) Prior Publication Data
US 2021/0188939 A1    Jun. 24, 2021

Related U.S. Application Data

(60) Provisional application No. 62/573,078, filed on Oct. 16, 2017.

(51) Int. Cl.
C07K 14/705    (2006.01)
A01K 67/027    (2006.01)
C12N 15/85    (2006.01)

(52) U.S. Cl.
CPC .......... *C07K 14/705* (2013.01); *A01K 67/027* (2013.01); *C12N 15/85* (2013.01)

(58) Field of Classification Search
None
See application file for complete search history.

(56) References Cited

U.S. PATENT DOCUMENTS

| | | | |
|---|---|---|---|
| 9,820,475 B2 | 11/2017 | Prather et al. | |
| 9,854,790 B2 | 1/2018 | Ait-Ali et al. | |
| 10,080,353 B2 | 9/2018 | Prather et al. | |
| 10,091,975 B2 | 10/2018 | Prather et al. | |
| 10,405,526 B2 | 9/2019 | Prather et al. | |
| 10,827,730 B2 | 11/2020 | Prather et al. | |
| 11,019,809 B2 | 6/2021 | Prather et al. | |
| 11,160,260 B2 | 11/2021 | Prather et al. | |
| 2011/0016546 A1 | 1/2011 | Bedell et al. | |
| 2017/0035035 A1* | 2/2017 | Prather | A01K 67/02 |

FOREIGN PATENT DOCUMENTS

| | | |
|---|---|---|
| CN | 101503688 A | 8/2009 |
| WO | WO-2019079285 A1 | 4/2019 |
| WO | WO-2020198541 A1 | 10/2020 |

OTHER PUBLICATIONS

Van Gorp, H., Van Breedam, W., Van Doorsselaere, J., Delputte, P.L. and Nauwynck, H.J., 2010. Identification of the CD163 protein domains involved in infection of the porcine reproductive and respiratory syndrome virus. Journal of virology, 84(6), pp. 3101-3105. (Year: 2010).*

Burkard et al. Pigs Lacking the Scavenger Receptor Cysteine-Rich Domain 5 of CD163 Are Resistant to Porcine Reproductive and Respiratory Syndrome Virus 1 Infection. Journal of Virology, vol. 92, Issue 16, e00415-18 (Aug. 2018). Accepted manuscript posted online Jun. 20, 2018. 13 pages.

Calvert et al. CD163 Expression Confers Susceptibility to Porcine Reproductive and Respiratory Syndrome Viruses. Journal of Virology, vol. 81, No. 14, pp. 7371-7379 (Jul. 2007). Published ahead of print May 9, 2007.

Dong et al. Associations of natural variation in the CD163 and other candidate genes on host response of nursery pigs to porcine reproductive and respiratory syndrome virus infection. Journal of Animal Science, 2021, vol. 99, No. 10, 1-19. Advance Access publication Sep. 27, 2021.

GenBank Accession No. AJ311716. Version No. AJ311716.1. Sus scrofa mRNA for putative CD163 antigen. Record created Jan. 7, 2003. 2 pages. Retrieved Nov. 20, 2023 at URL: https://www.ncbi.nlm.nih.gov/nuccore/AJ311716.1/.

GenBank Accession No. EU016226. Version No. EU016226.1. Sus scrofa CD163 mRNA, complete cds. Record created Sep. 4, 2008. 2 pages. Retrieved Nov. 20, 2023 at URL: https://www.ncbi.nlm.nih.gov/nuccore/EU016226.1/.

Graversen et al. CD163: a signal receptor scavenging haptoglobin-hemoglobin complexes from plasma. The International Journal of Biochemistry & Cell Biology 34 (2002) 309-314.

Guo et al. Modulation of CD163 Expression by Metalloprotease ADAM17 Regulates Porcine Reproductive and Respiratory Syndrome Virus Entry. Journal of Virology, vol. 88, No. 18, pp. 10448-10458 (Sep. 2014). Published ahead of print Jun. 25, 2014.

(Continued)

*Primary Examiner* — Neil P Hammell
*Assistant Examiner* — Khaleda B Hasan
(74) *Attorney, Agent, or Firm* — Tracey S. Truitt; Sandberg Phoenix & von Gontard, PC

(57) ABSTRACT

The present disclosure provides compositions and methods for decreasing permissiveness to infection by PRRSV. The methods involve inserting peptides or oligopeptides into the CD163 SRCR domain 5 to disrupt the protein structure and thereby prevent PRRSV infection. The deletion of the exon 13 region of PSTII eliminates infection. The replacement of cysteine residues with alanines in SRCR5 as a means to disrupt disulfide bond formation. The final method is the deletion of, or amino acid substitution within the SRCR4-5 interdomain region.

4 Claims, 6 Drawing Sheets

Specification includes a Sequence Listing.

(56) References Cited

OTHER PUBLICATIONS

Ma et al. The Crystal Structure of the Fifth Scavenger Receptor Cysteine-Rich Domain of Porcine CD163 Reveals an Important Residue Involved in Porcine Reproductive and Respiratory Syndrome Virus Infection. Journal of Virology, vol. 91, Issue 3, e01897-16 (Feb. 2017). Accepted manuscript posted online Nov. 23, 2016. 15 pages.
PCT/US2018/056065 International Search Report and Written Opinion dated Feb. 25, 2019.
Van Gorp et al. Sialoadhesin and CD163 join forces during entry of the porcine reproductive and respiratory syndrome virus. Journal of General Virology (2008), 89, 2943-2953.
Allende, et al. North American and European Porcine Reproductive and Respiratory Syndrome Viruses Differ in Non-structural Protein Coding Regions. Journal of General Virology. vol. 80 (1999): 9 pages.
Benfield, et al. Characterization of Swine Infertility and Respiratory Syndrome (SIRS) Virus (isolate ATCC VR-2332). Journal of Veterinary Diagnostic Investigation. vol. 4, Issue 2 (1992): 7 pages.
Bullido, et al. Monoclonal Antibodies Specific for Porcine Monocytes/Macrophages: Macrophage Heterogeneity in the Pig Evidenced by the Expression of Surface Antigens. Tissue Antigens. vol. 49, Issue 4 (1997): 11 pages.
Burkard, et al. Precision Engineering for PRRSV Resistance in Pigs: Macrophages from Genome Edited Pigs Lacking CD163 SRCR5 Domain are Fully Resistant to Both PRRSV Genotypes While Maintaining Biological Function. PLoS Pathogens. vol. 13, Issue 2 (2017): 28 pages.
Cafruny, et al. Antibiotic-Mediated Inhibition of Porcine Reproductive and Respiratory Syndrome Virus (PRRSV) Infection: A Novel Quinolone Function Which Potentiates the Antiviral Cytokine Response in MARC-145 Cells and Pig Macrophages. Virology: Research and Treatment. vol. 1 (2008): 12 pages.
Chen et al. Generation of Pigs Resistant to Highly Pathogenic-Porcine Reproductive and Respiratory Syndrome Virus Through Gene Editing of CD163. International Journal of Biological Sciences. vol. 15, Issue 2 (2019): 12 pages.
Collins, et al. Isolation of Swine Infertility and Respiratory Syndrome Virus (isolate ATCC VR-2332) in North America and Experimental Reproduction of the Disease in Gnotobiotic Pigs. Journal of Veterinary Diagnostic Investigation. vol. 4, Issue 2 (1992): 10 pages.
Duan, et al. Virus Quantification and Identification of Cellular Targets in the Lungs and Lymphoid Tissues of Pigs at Different Time Intervals after Inoculation with Porcine Reproductive and Respiratory Syndrome Virus (PRRSV). Veterinary Microbiology. vol. 56, Issue 1-2 (1997): 11 pages.
Etzerodt, et al. Structural Basis for Inflammation-driven Shedding of CD163 Ectodomain and Tumor Necrosis Factor-α in Macrophages. Journal of Biological Chemistry. vol. 289, Issue 2 (2014): 11 pages.
Fabriek, et al. The Macrophage CD163 Surface Glycoprotein is an Erythroblast Adhesion Receptor. Blood. vol. 109, Issue 12 (2007): 7 pages.
Fabriek, et al. The Macrophage Scavenger Receptor CD163. Immunobiology. vol. 210, Issue 2-4 (2005): 8 pages.
Guo, et al. Highly Efficient Generation of Pigs Harboring a Partial Deletion of the CD163 SRCR5 Domain, Which are Fully Resistant to Porcine Reproductive and Respiratory Syndrome Virus 2 Infection. Frontiers in Immunology. vol. 10 (2019): 14 pages.
Halbur, et al. Comparative Pathogenicity of Nine US Porcine Reproductive and Respiratory Syndrome Virus (PRRSV) Isolates in a Five-week-old Cesarean-derived, Colostrum-deprived Pig Model. Journal of Veterinary Diagnostic Investigation. vol. 8, Issue 1 (1996): 10 pages.
Halbur, et al. Update on Abortion Storms and Sow Mortality. Swine Health and Production. vol. 5, Issue 2 (1997): 1 page.
Kappes, et al. PRRSV Structure, Replication and Recombination: Origin of Phenotype and Genotype Diversity. Virology (2015). 12 pages.
Kittawornrat, et al. Porcine Reproductive and Respiratory Syndrome Virus (PRRSV) Surveillance using Pre-weaning Oral Fluid Samples Detects Circulation of Wild-type PRRSV. Veterinary Microbiology. vol. 168, Issue 2-4 (2014): 9 pages.
Kristiansen, et al. Identification of the Haemoglobin Scavenger Receptor. Nature. vol. 409, Issue 6817 (2001): 4 pages.
Kuhn, et al. Reorganization and Expansion of the Nidoviral Family Arteriviridae. Archives of Virology. vol. 161, Issue 3 (2016): 14 pages.
Ladinig, et al. Pathogenicity of Three Type 2 Porcine Reproductive and Respiratory Syndrome Virus Strains in Experimentally Inoculated Pregnant Gilts. Virus Research. vol. 203 (2015): 12 pages.
Lamontagne, et al. Porcine Reproductive and Respiratory Syndrome Virus Persistence in Blood, Spleen, Lymph Nodes, and Tonsils of Experimentally Infected Pigs Depends on the Level of CD8high T Cells. Viral Immunology. vol. 16, Issue 3 (2003): 12 pages.
Law, et al. A New Macrophage Differentiation Antigen Which is a Member of the Scavenger Receptor Superfamily. European Journal of Immunology. vol. 23, Issue 9 (1993): 6 pages.
Lee, et al. A DNA-launched Reverse Genetics System for Porcine Reproductive and Respiratory Syndrome Virus Reveals that Homodimerization of the Nucleocapsid protein is Essential for Virus Infectivity. Virology. vol. 331, Issue 1 (2005): 16 pages.
Lee, et al. Generation of a Porcine Alveolar Macrophage Cell Line for the Growth of Porcine Reproductive and Respiratory Syndrome Virus. Journal of Virological Methods. vol. 163, Issue 2 (2010): 6 pages.
Madson, et al. Molecular Characterization of the Haptoglobin. hemoglobin Receptor CD163. Ligand Binding Properties of the Scavenger Receptor Cysteine-rich Domain Region. vol. 279, Issue 49 (2004): 8 pages.
Meulenberg, et al. Lelystad Virus, The Causative Agent of Porcine Epidemic Abortion and Respiratory Syndrome (PEARS), Is related to LDV and EAV. Virology. vol. 192, Issue 1 (1993): 11 pages.
Nelson, et al. Porcine Reproductive and Respiratory Syndrome Virus Comparison: Divergent Evolution on Two Continents. Journal of virology. vol. 73, Issue 1 (1999): 11 pages.
Onofre, et al. Scavenger Receptor CD163 and its Biological Functions. Acta Medica (Hradec Kralove). vol. 52, Issue 2 (2009): 5 pages.
Pasternak, et al. Development and Application of a Porcine Specific ELISA for the Quantification of Soluble CD163. Veterinary Immunology and Immunopathology. vol. 210 (2019): 8 pages.
Patton, et al. Modulation of CD163 Receptor Expression and Replication of Porcine Reproductive and Respiratory Syndrome Virus in Porcine Macrophages. Virus research. vol. 140, Issue 1-2 (2009): 11 pages.
Pei, et al. Porcine Reproductive and Respiratory Syndrome Virus as a Vector: Immunogenicity of Green Fluorescent Protein and Porcine Circovirus Type 2 Capsid Expressed from Dedicated Subgenomic RNAs. Virology. vol. 389. Issue 1-2 (2009): 9 pages.
Popescu, et al. Genetically Edited Pigs Lacking CD163 Show No. Resistance Following Infection with the African Swine Fever Virus Isolate, Georgia 2007/1. Virology. vol. 501 (2017): 5 pages.
Prather, et al. Knockout of Maternal CD163 Protects Fetuses from Infection with Porcine Reproductive and Respiratory Syndrome Virus (PRRSV). Scientific Reports. vol. 7, Issue 1 (2017): 5 pages.
Ritter, et al. Genomic Organization and Chromosomal Localization of the Human CD163 (M130) Gene: A Member of the Scavenger Receptor Cysteine-rich Superfamily. Biochemical and Biophysical Research Communications. vol. 260, Issue 2 (1999): 9 pages.
Sanchez-Torres, et al. Expression of Porcine CD163 on Monocytes/Macrophages Correlates with Permissiveness to African Swine Fever Infection. Archives of Virology. vol. 148, Issue 12 (2003): 17 pages.
Snijder, et al. The Molecular Biology of Arteriviruses. Journal of General Virology. vol. 79 (1998): 19 pages.
Stoian, et al. Identification of CD163 Regions that are Required for Porcine Reproductive and Respiratory Syndrome Virus (PRRSV)

(56) References Cited

OTHER PUBLICATIONS

Infection but not for Binding to Viral Envelope Glycoproteins. Virology. vol. 574 (2022): 13 pages.

Stoian, et al. Mutations within Scavenger Receptor Cysteine-rich (SRCR) Protein Domain 5 of Porcine CD163 Involved in Infection with Porcine Reproductive and Respiratory Syndrome Virus (PRRS). Journal of General Virology. vol. 103 (2022): 18 pages.

Subramanian, et al. CD163 and IgG Codefend Against Cytotoxic Hemoglobin via Autocrine and Paracrine Mechanisms. The Journal of Immunology. vol. 190, Issue 10 (2013): 12 pages.

Van Gorp, et al. Scavenger Receptor CD163, A Jack-of-all-trades and Potential Target for Cell-directed Therapy. Molecular Immunology. vol. 47, Issue 7-8 (2010): 11 pages.

Wang, et al. Emergence of a Virulent Porcine Reproductive and Respiratory Syndrome Virus in Vaccinated Herds in the United States. Virus Research. vol. 210 (2015): 34-41.

Wang, et al. Immune Responses in Piglets Infected with Highly Pathogenic Porcine Reproductive and Respiratory Syndrome Virus. Veterinary Immunology and Immunopathology. vol. 142, Issue 3-4 (2011): 9 pages.

Wang, et al. PK-15 Cells Transfected with Porcine CD163 by PiggyBac Transposon System are Susceptible to Porcine Reproductive and Respiratory Syndrome Virus. Journal of Virological Methods. vol. 193, Issue 2 (2013): 8 pages.

Wells, et al. Replacement of Porcine CD163 Scavenger Receptor Cysteine-Rich Domain 5 with a CD163-Like Homolog Confers Resistance of Pigs to Genotype 1 but Not Genotype 2 Porcine Reproductive and Respiratory Syndrome Virus. Journal of Virology. vol. 91, Issue 2 (2017): 11 pages.

Wensvoort, et al. Mystery Swine Disease in The Netherlands: The Isolation of Lelystad Virus. Veterinary Quarterly. vol. 13, Issue 3 (1991): 10 pages.

Whitworth, et al. Gene-edited Pigs are Protected from Porcine Reproductive and Respiratory Syndrome Virus. Nature Biotechnology. vol. 34, Issue 1 (2016): 3 pages.

Whitworth, et al. Use of the CRISPR/Cas9 System to Produce Genetically Engineered Pigs from in Vitro-derived Oocytes and Embryos. Biology of Reproduction. vol. 91, Issue 3 (2014): 13 pages.

Workman, et al. Evaluating Large Spontaneous Deletions in a Bovine Cell Line Selected for Bovine Viral Diarrhea Virus Resistance. Viruses. vol. 13 (2021): 17 pages.

Yang, et al. CD163 Knockout Pigs are Fully Resistant to Highly Pathogenic Porcine Reproductive and Respiratory Syndrome Virus. Antiviral Research. vol. 151 (2018): 63-70.

Yu, et al. CD163ASRCR5 MARC-145 Cells Resist PRRSV-2 Infection via Inhibiting Virus Uncoating, Which Requires the Interaction of CD163 With Calpain 1. Frontiers in Microbiology. vol. 10 (2020): 16 pages.

Zhu, et al. TREM2 Suppresses the Proinflammatory Response to Facilitate PRRSV Infection Via PI3K/NF-κB Signaling. PLoS Pathogens. vol. 16, Issue 5 (2020): 28 pages.

Zimmerman, et al. Porcine Reproductive and Respiratory Syndrome Viruses (Porcine Arteriviruses). Diseases of Swine (2019): 24 pages.

\* cited by examiner

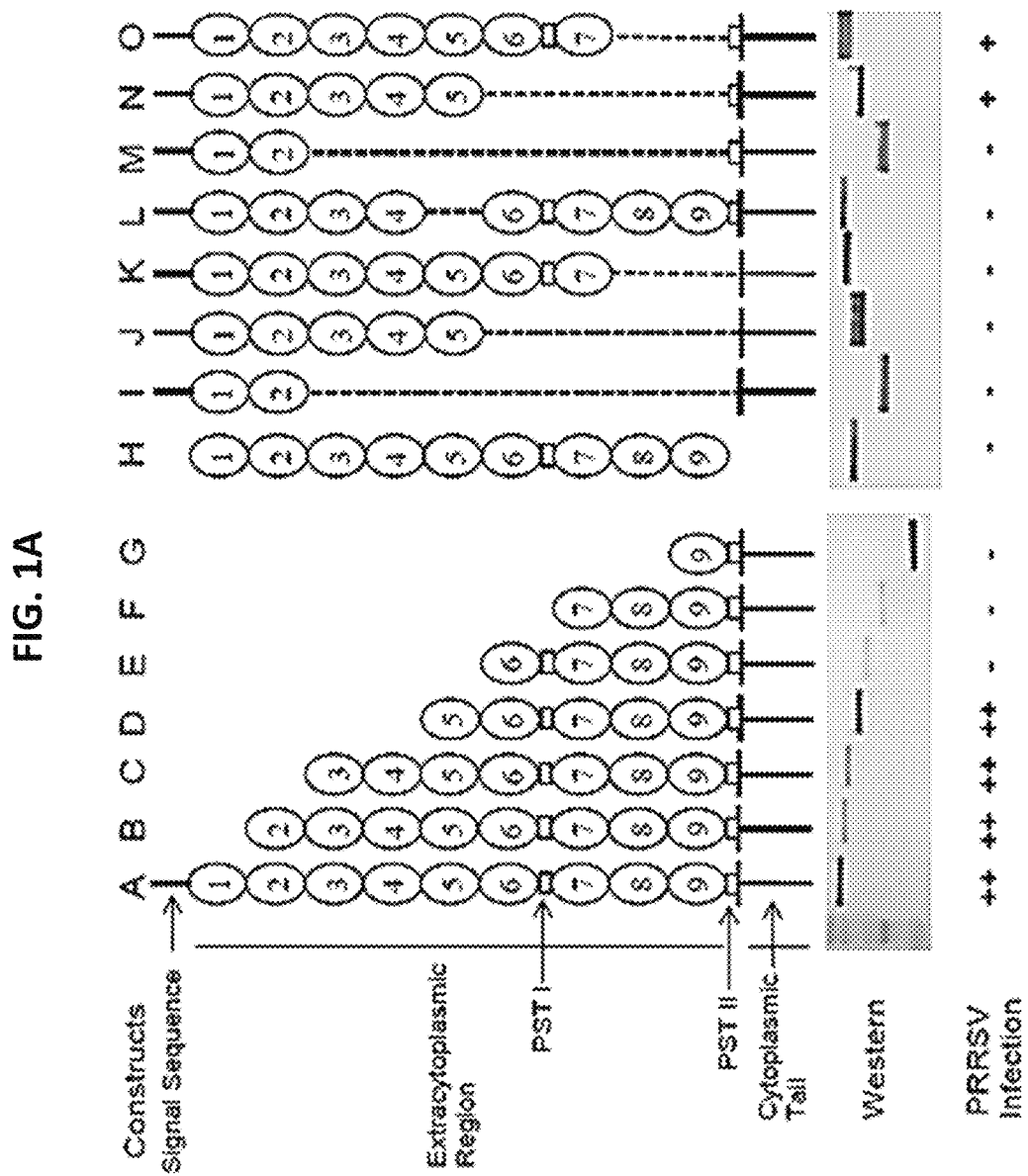

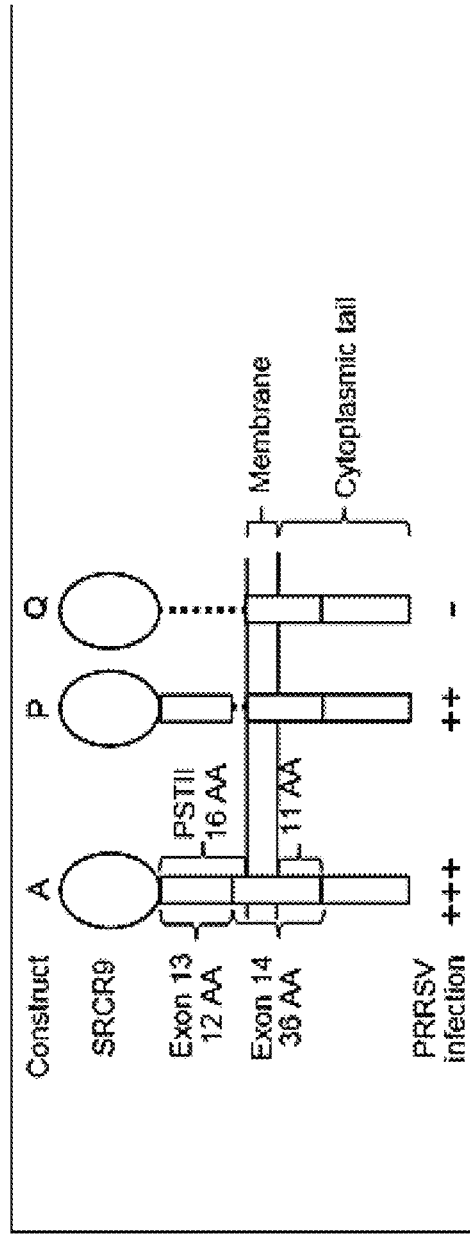
FIG. 2A
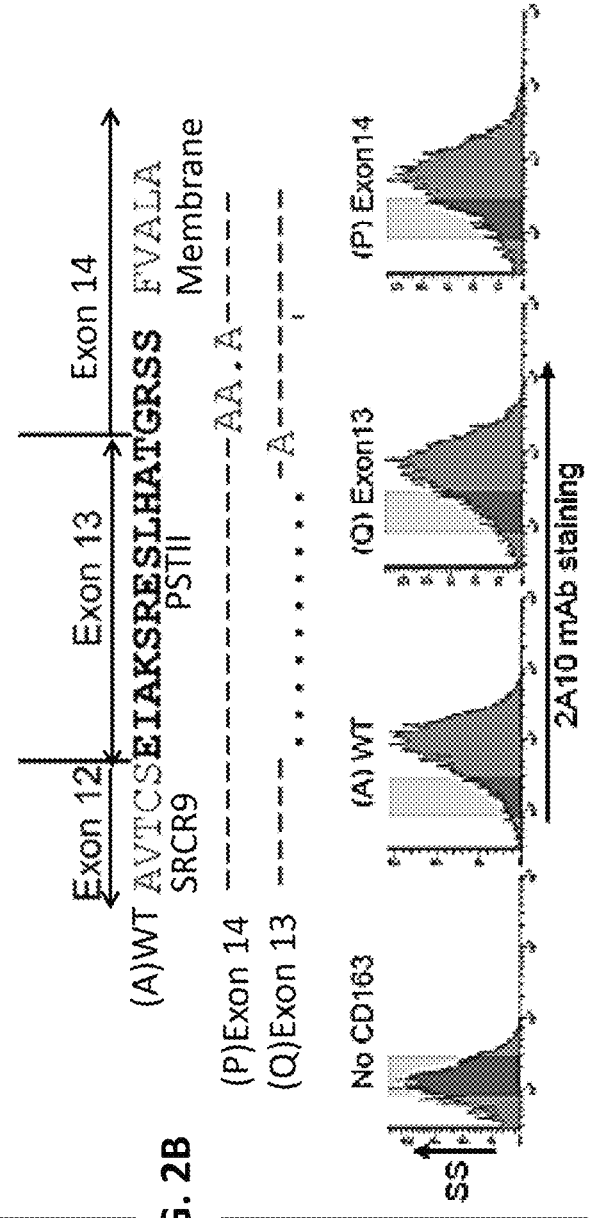
FIG. 2B
FIG. 2C

METHODS AND COMPOSITIONS FOR TREATING AND PROTECTING AGAINST PORCINE REPRODUCTIVE AND RESPIRATORY SYNDROME VIRUS

GOVERNMENT LICENSE RIGHTS

This invention was made with government support under USDA-NIFA 2017-67015-26774 awarded by The U.S. Department of Agriculture. The government has certain rights in the invention.

SEQUENCE LISTING

The instant application contains a Sequence Listing which has been submitted electronically in ASCII format and is hereby incorporated by reference in its entirety. Said ASCII copy, created on Apr. 16, 2020, is named 40423-PCT_ST25 (22532255.1).txt and is 17,063 bytes in size.

FIELD

The present disclosure relates to compositions for treating and protecting against porcine reproductive and respiratory syndrome virus and methods of using these compositions. Additionally, the disclosure provides for methods of detecting the compositions.

BACKGROUND

Initially described in the USA in 1987 as the "mystery swine disease", porcine reproductive and respiratory syndrome (PRRS) is now endemic in many swine-producing countries. The principal impacts of infection are reproductive failure, poor growth performance, and respiratory disease in young pigs. The causative agent, porcine reproductive and respiratory syndrome virus (PRRSV), was first isolated and sequenced in The Netherlands in 1991 and named Lelystad virus. Soon afterwards, VR-2332 was isolated and sequenced in North America. North American (NA) and European (EU) PRRSV isolates represent two distinct genotypes, which share only about 70% identity at the nucleotide level. Recently, the nomenclature was modified to designate the prototype EU isolates as PRRSV-1 and NA isolates as PRRSV-2.

PRRSV is a small, enveloped positive-sense single-stranded RNA virus from the order Nidovirales, family Arteriviridae, genus Arterivirus and has a restricted host and cell tropism for cells of the monocyte-macrophage lineage.

The main receptor for PRRSV on macrophages is CD163, a 130 kDa PRRSV-I transmembrane protein. The gene contains 17 exons, which code for a peptide signal sequence followed by nine scavenger receptor cysteine-rich (SCR) domains, with SRCR6 and 7 separated by a proline-serine-threonine rich (PST) polypeptide of approximately 35 amino acids. Following the SRCR domains, a short, 16 amino acid PST linker domain (PSTII) connects SRCR9 with a transmembrane domain and an intracellular cytoplasmic tail. Currently, only SRCR2, SRCR3 and SRCR5 have been found to be involved in biological processes. A 13-amino-acid motif within SRCR2 mediates erythroblast binding and interacts with both Gram-positive and Gram-negative bacteria. In addition, hemoglobin-haptoglobin (Hb-Hp) complexes are internalized after binding to SRCR3. In 2003, CD163 was described as a putative receptor for African swine fever virus (ASFV). This conclusion was based on the observation that infected macrophages possess a mature CD163-positive phenotype combined with the capacity of anti-CD163 monoclonal antibodies to reduce ASFV infection of primary alveolar macrophages in culture. However, genetically modified pigs lacking CD163 are susceptible to infection by the ASFV Georgia/07 isolate. In 2007 Calvert et al. described CD163 as a receptor for PRRSV. Transfection with CD163 cDNAs from simian, human, canine, and mouse origins rendered a variety of non-permissive cell lines fully permissive to PRRSV-2 PRRSV infection, including the production of progeny virus. Subsequently, in 2010 Van Gorp et al. mapped the individual SRCR domains involved in determining permissiveness of a PRRSV-1 genotype virus. The experimental design was based on the transfection of non-permissive HEK293T cells with cDNAs possessing various SRCR domain deletions and/or substitutions with domain homologs from human CD163-like 1 protein (hCD163L1). Cells transfected with CD163 cDNA possessing a swap between SRCR5 and the hCD163L1 homolog, SRCR8, were not permissive after infection with a genotype 1 virus (PRRSV-1), identifying SRCR5 as the domain involved in PRRSV infection by PRRSV-1 viruses. Recently, we showed that genetically modified (GM) pigs lacking CD163 expression on macrophages fail to support infection with both genotype 1 and 2 (PRRSV-2) viruses. Furthermore, the substitution of CD163 SRCR5 with the hCD163L1 homolog, SRCR8, conferred resistance of macrophages and pigs to infection with PRRSV-1 viruses confirming the results of Van Gorp et al., 2010. However, pigs retain the ability to support replication after infection with PRRSV-2 viruses. Together these results showed that PRRSV-1 and PRRSV-2 viruses possess distinct differences in the recognition of the CD163 protein.

The importance of SRCR5 for infection with PRRSV-2 viruses was demonstrated by two recent reports. In 2016, Ma et al. carried out structure-based studies, which located an arginine residue at position 561 (Arg561) within SRCR5 as important for PRRSV infection. More recently, Burkard et al. showed that porcine alveolar macrophages (PAMs) or peripheral blood monocyte-derived macrophages (PMMs) from GM pigs possessing a complete deletion of SRCR5 are resistant to both PRRSV-1 and PRRSV-2 viruses.

SUMMARY

The overall goal was to identify the minimum changes in CD163 sufficient to make cells resistant to infection with a genotype 2 PRRSV. The study identified domains in CD163, which are involved in infection by PRRSV-2 PRRSV. The results demonstrate a requirement for SRCR5 and PSTII as necessary for infection. Within PSTII, the deletion of 12 amino acids encoded by exon 13 prevents infection without affecting the expression of CD163 on the surface of the cell. The deletion of SRCR8 and 9 domains have a lesser effect on infection. The mapping of peptide domains within SRCR5 show that the insertion of proline-arginine (PR) after amino acids 8, 54 and 99, inhibit infection. Furthermore, the deletion of individual disulfide bonds by the replacement of cysteine residues with alanines also inhibits infection. And finally, the deletion of, or amino acid substitution within the SRCR4-5 interdomain sequence, AHRK (SEQ ID NO. 64), also blocks infection. Together, these mutant constructs provide a means to express CD163 receptors that are resistant to PRRSV infection.

The CD163 constructs used to study mutations within CD163 are described in FIGS. 1, 2, and 3. FIG. 1 shows the effect of the domain deletions in CD163 on the infection of HEK cells. The peptide sequence referred to in FIG. 1 is from GenBank No. AJ311716. The experimental system used to study infection incorporated a plasmid that contained CD163 fused to EGFP. After transfection into PRRSV non-permissive HEK cells, the expression of CD163 is apparent by the presence of green fluorescence. The PRRSV-2 virus used in this study, PRRSV-RFP, expressed red fluorescence in infected cells. Therefore, after infection of transfected HEK cells, the presence of red fluorescence in a green cell is a positive result. The truncated CD163 cDNA fragments shown in FIG. 1 were prepared by PCR amplification of the pcDNA template using the GoTaqGreen® Master Mix (Promega) according to manufacturer's instructions. PCR conditions included 95° C. for 2 minutes, followed by 30 cycles of 94 °C for 30 seconds, 65° C. for 30 seconds, and 72 °C for 2 minutes, and a final extension at 72° C. for 10 minutes. The PCR primers for constructs shown in FIG. 1 as well as some other constructs are listed in Table 1. The PCR products were cloned into pCR®2.1-TOPO® vector (Invitrogen) and transformed into One Shot™ TOP10 chemically competent E. coli cells (Invitrogen). The purified plasmids were double-digested with KpnI and XbaI and cloned into the KpnI-XbaI sites of the pcDNA3.1-EGFP vector. Plasmids were transfected into HEK cells using FuGENE® HD reagent (Promega) according to manufacturer's instructions and viewed for the presence of EGFP expression under a fluorescence microscope. The resulting N-terminally truncated CD163 proteins are illustrated in FIG. 1A (constructs B through G).

Constructs that possessed deletions in domains from the C-terminal end of CD163 incorporated primers that possessed PacI restriction sites, which are listed in Table 1. Deletions were made using a long PCR protocol designed to amplify the desired CD163 fragment along with the entire pcDNA3.1-EGFP plasmid. PCR amplification was performed using LongAmp® Taq DNA Polymerase (New England Biolabs Inc). PCR conditions included 94° C. for 30 s, followed by 30 cycles of 94° C. for 30 s, 65° C. for 1 min, and 65° C. for 8 min, followed by a final extension at 65° C. for 10 min. The PCR products were cut with PacI and the plasmid re-circularized by ligation with Anza™ T4 DNA Ligase Master Mix (Invitrogen), and then transfected into HEK cells. The resulting CD163 deletion constructs retained intact transmembrane and cytoplasmic domains along with an added PacI site.

TABLE 1

Primers for amplification of CD163 constructs shown in FIG. 1 (underlined nucleotides identify restriction sites)

| | | |
|---|---|---|
| B | FW: | GGTACCATGGGATCTGATTTAGAGATGAGG-SEQ ID NO. 25 |
| | RV: | TCTAGATTGTACTTCAGAGTGGTC TCC-SEQ ID NO. 26 |
| C | FW: | GGTACCATGGGAGCAGACCTGAAACTG-SEQ ID NO. 27 |
| | RV: | TCTAGATTGTACTTCAGAGTGGTC TCC-SEQ ID NO. 26 |
| D | FW: | GGTACCATGCACAGGAAACCCAGGC-SEQ ID NO. 28 |
| | RV: | TCTAGATTGTACTTCAGAGTGGTC TCC-SEQ ID NO. 26 |
| E | FW: | GGTACCATGTACACACAAATCCGC-SEQ ID NO. 29 |
| | RV: | TCTAGATTGTACTTCAGAGTGGTC TCC-SEQ ID NO. 26 |
| F | FW: | GGTACCATGAGTGGTCAACTTCGCCTG-SEQ ID NO. 30 |
| | RV: | TCTAGATTGTACTTCAGAGTGGTC TCC-SEQ ID NO. 26 |
| G | FW: | GGTACCATGAAAATAAGACTTCAAGAAGGAAACACT-SEQ ID NO. 31 |
| | RV: | TCTAGATTGTACTTCAGAGTGGTC TCC-SEQ ID NO. 26 |
| H | FW: | GGTACCATGGGAAAAGACAAGGAG-SEQ ID NO. 32 |
| | RV: | TCTAGATTCTGAGCACGTCACAGC-SEQ ID NO. 33 |
| I | FW: | ATTATTAATTAAGTTTGTTGCACTTGCAATCTTTGGGGT-SEQ ID NO. 34 |
| | RV: | ATCATTAATTAAATTTAAGCAAATCACTCCAGCATCCTCAG-SEQ ID NO. 35 |
| J | FW: | ATTATTAATTAAGTTTGTTGCACTTGCAATCTTTGGGGT-SEQ ID NO. 34 |
| | RV: | ATCGTTAATTAATCTTGAGCAGACTACGCCG-SEQ ID NO. 36 |
| K | FW: | ATTATTAATTAAGTTTGTTGCACTTGCAATCTTTGGGGT-SEQ ID NO. 34 |
| | RV: | CAGTTTAATTAACTCTGAGCAGATGACTCCTGC-SEQ ID NO. 37 |
| L | FW: | CACTTTAATTAAGTACACACAAATCCGCTTGGTGAATG-SEQ ID NO. 38 |
| | RV: | CATATTAATTAAGGCTGAGCAGGTAATTTTGGCTTC-SEQ ID NO. 39 |
| M | FW: | ATTATTAATTAAGATTGCAAAGAGCCGAGAATCCCTACATG-SEQ ID NO. 40 |
| | RV: | ATCATTAATTAAATTTAAGCAAATCACTCCAGCATCCTCAG-SEQ ID NO. 41 |
| N | FW: | ATTATTAATTAAGATTGCAAAGAGCCGAGAATCCCTACATG-SEQ ID NO. 40 |
| | RV: | ATCGTTAATTAATCTTGAGCAGACTACGCCG-SEQ ID NO. 42 |
| O | FW: | ATTATTAATTAAGATTGCAAAGAGCCGAGAATCCCTACATG-SEQ ID NO. 40 |
| | RV: | CAGTTTAATTAACTCTGAGCAGATGACTCCTGC-SEQ ID NO. 37 |
| P | FW: | CACACCGCGGCTTTTGTTGCACTTGCAATCTTTGGGGTCATTCTGT-SEQ ID NO. 21 |
| | RV: | CCCACCGCGGCTGTGGCATGTAGGGATTCTCGGCTCTTT-SEQ ID NO. 22 |

TABLE 1-continued

Primers for amplification of CD163 constructs shown in FIG. 1 (underlined nucleotides identify restriction sites)

| | | |
|---|---|---|
| Q | FW: | CACA<u>CCGCGG</u>GTCGCTCATCTTTTGTTGCACTT GCAATCTTT-SEQ ID NO. 23 |
| | RV: | AACA<u>CCGCGG</u>CTGAGCACGTCACAGCAGCATCCT-SEQ ID NO. 24 |
| C7 to A | FW: | CAAC<u>CCGCGG</u>CCTGACGGGACAGCCAGCCAC-SEQ ID NO. 55 |
| | RV: | ACAA<u>CCGCGG</u>TGCTACTGGGCAGAGTGAAAGGTGGGACTC-SEQ ID NO. 56 |

The CD163-EGFP deletion constructs transfected into HEK cells are illustrated in FIG. 1a. All constructs showed EGFP fluorescence within 24 hrs after transfection of plasmids. Western blots stained with anti-GFP confirmed that each construct migrated according to the predicted size (FIG. 1b). HEK cells transfected with the full-length CD163-EGFP fusion plasmid, Construct A, served as a positive control for infection with the P129-RFP virus. A plasmid expressing a soluble form of CD163-EGFP, Construct H, was included as a negative infection control. The N-terminal truncation mutants are identified as constructs B-G in FIG. 1A. Constructs A-D, which contained SRCR5 were positive for infection. The remaining N-terminal deletion mutants, constructs E-G, which lacked SRCR5, were negative for infection. The results for the C-terminal deletions lacking PSTII, constructs I through K, were all negative for infection, including the constructs J and K, which retained the SRCR5 domain. Constructs N and O, which were identical to J and K, except for the addition of the PSTII domain, were positive for infection. When taken together, all of the constructs in FIG. 1a lacking SRCR5 or PSTII were negative for infection. These results indicate that the presence of SRCR5 and/or PSTII is required for infection.

The CD163 PSTII partial and complete deletion constructs were amplified by incorporating primers that possessed SacII restriction sites. The SacII sites were placed in the frame that would result in desired deletion along with the insertion or substitution of alanines. The primers used for amplification are listed in Table 1. The 16 amino acid PSTII domain (SEQ ID NO. 57) can be divided into two regions. The exon 14 portion consists of the four amino acids, GRSS (SEQ ID NO. 55) (see FIG. 2B). The remainder of exon 14 includes the transmembrane domain and a portion of the cytoplasmic tail. The substitution of GRSS (SEQ ID NO. 21-22) in SEQ ID NO. 55 with three alanines (Construct P) resulted in only a small reduction in infection. The removal of 10 amino acids within the exon 13 (SEQ ID NO. 23-24) (SEQ ID NO. 78) region completely blocked infection. The results in FIG. 2C showed that all constructs were expressed on the surface of transfected HEK cells. Therefore, the deletion of the region of CD163 encoded by exon 13 is sufficient to prevent infection.

The role of individual mutations in SRCR5 in the permissiveness of CD163 for PRRSV infection is illustrated in FIG. 3. The peptide sequence number is above the sequence with the CD163 peptide sequence coordinates in parentheses. The arrows show the location and direction of beta sheets and the dotted lines, the location of alpha helices. The asterisks show the location of SacII (proline-arginine) insertions. Primers containing SacII restriction site insertions were used to PCR amplify the CD163 plasmid (see Table 2). The restriction sites were placed in the same coding frame as the CD163 peptide sequence. The resulting PCR products were cut with SacII and then re-ligated to restore the circular plasmid. The six base pair SacII restriction site, CCG CGG (SEQ ID NO. 56), when placed in frame, codes for a proline-arginine dipeptide. The purpose for inserting a proline-arginine is to disrupt protein secondary structure. In addition, arginine contains a charged R-group. When placed in the right position within domain 5, the insertion of the dipeptide would be sufficient to disrupt the primary or secondary structure of domain 5 and prevent recognition by PRRSV. The presence of a SacII site provides a convenient means to test for the presence of the genomic modification. Recombinant plasmids were transfected into HEK cells. The infection results for the different SacII restriction site insertions are presented in Table 2. The results showed a wide variation in the infection levels of the different constructs. For the purpose of comparison, the relative number of infected cells was compared to HEK cells transfected with the wild type (WT—unmodified) CD163 (SEQ ID NO. 60). As can be seen, all of the tested constructs were resistant to PRRSV infection in comparison to the unmodified CD163 (control). Constructs, such as PR-15, PR-62, PR-78 and PR-89 showed a level of infection that was slightly less than the positive control. In contrast, other constructs showed greatly reduced levels of infection. Three constructs, PR-9, PR-55 and PR-100, showed only a few infected cells. These constructs are considered the most "resistant" to PRRSV infection. When inserted into the genome of a pig, these insertions should constitute and confer a significant degree of resistance to PRRSV.

TABLE 2

Primer sequence for the preparation of constructs in FIG. 3 (SacII restriction site is underlined).

| SRCR5 Construct | PCR Primers | HEK Infection |
|---|---|---|
| None[*1] | Unmodified CD163-SEQ ID NO. 60 | ++++[*2] |
| PR-9 | F-ATTA<u>CCGCGG</u>CCCTGCTCTGGTCGTGTTG-SEQ ID NO. 3<br>R-ATTA<u>CCGCGG</u>AATGTCCCCTCCAACCAGCC-SEQ ID NO. 4 | +/− |
| PR-15 | F-CAC<u>CCCGCGGG</u>AAGTACAACATGGAGACACGTGGGG-SEQ ID NO. 43<br>R-ACCA<u>CCGCGG</u>AACACGACCAGAGCAGGGAATGTC-SEQ ID NO. 44 | +++ |

TABLE 2-continued

Primer sequence for the preparation of constructs in FIG. 3 (SacII restriction site is underlined).

| SRCR5 Construct | PCR Primers | HEK Infection |
|---|---|---|
| PR-22 | F-ATTACCGCGGTGGGGCACCGTCTGTGATTC-SEQ ID NO. 5<br>R-GTGACCGCGGCGTGTCTCCATGTTGTACTTCAAC-SEQ ID NO. 6 | + |
| PR-32 | F-TATACCGCGGCTGGAGGCGGCCAGCGT-SEQ ID NO. 7<br>R-CGCTCCGCGGAGAGAAGTCAGAATCACAGACGGTGC-SEQ ID NO. 8 | + |
| PR-38 | F-GATACCGCGGCTGTGCAGGGAACTACAGTGCGGCACT-SEQ ID NO. 45<br>R-TATACCGCGGCACGCTGGCCGCCTCCAGAGAGAA-SEQ ID NO. 46 | ++ |
| PR-42 | F-ATCCCCGCGGCTACAGTGCGGCACTGTGGTTTCC-SEQ ID NO. 9<br>R-ATCACCGCGGTTCCCTGCACAGCACGCTGGC-SEQ ID NO. 10 | ++ |
| PR-55 | F-CAACCCGCGGCACTTTGGAGAAGGAAGTGGACAGATCTGGGC-SEQ ID NO. 11<br>R-ACACCCGCGGAGCTCCCCCCAGGAGGGAAACCAC-SEQ ID NO. 12 | +/- |
| PR-62 | F-CAACCCGCGGCAGATCTGGGCTGAAGAATTCCAGTGT-SEQ ID NO. 53<br>R-CACACCGCGGTCCACTTCCTTCTCCAAAGTGAGCTCCC-SEQ ID NO. 54 | +++ |
| PR-67 | F-CACCCCGCGGGAATTCCAGTGTGAGGGGCACGAG-SEQ ID NO. 13<br>R-ACCCCCGCGGTTCAGCCCAGATCTGTCCACTTCC-SEQ ID NO. 14 | + |
| PR-78 | F-AAGGCCGCGGTCACTCTGCCCAGTAGCACCCC-SEQ ID NO. 15<br>R-CACACCGCGGAAGGTGGGACTCGTGCCCCTCACA-SEQ ID NO. 16 | +++ |
| PR-89 | F-CCGACCGCGGACATGTAGCCACAGCAGGGACGTC-SEQ ID NO. 17<br>R-TATACCGCGGCCCGTCAGGGCGGGGTGC-SEQ ID NO. 18 | +++ |
| PR-100 | F-CGCGCCGCGGTGCTCAAGATACACACAAATCCGC-SEQ ID NO. 19<br>R-CAACCCGCGGGACTACGCCGACGTCCCTGC-SEQ ID NO. 20 | +/- |

*[1]The number shows the nucleotide number with amino acid position in parentheses.
*[2]Key: ++++, infection of multiple cells with foci containing clusters of infecte cells; +++, fewer number of infected cells, but still possessing foci containing clusters of infected cells; ++, several single cells infected with virus; + a small number of cells showing infection; +/- only one or two infected cells in the well.

The predicted locations of the PR-9, PR-55 and PR-100 mutations on the surface of the SRCR5 structure are shown in FIG. 4a. A space-filling model showed that the three mutations were located on a single face of the SRCR5 polypeptide, in close proximity to the LBP and the loop 5-6 region previously described by Van Gorp et al., 2010 and Graversen et al., 2002 as potential CD163-PRRSV contact regions. Even though the PR-9 and PR-100 mutations are located at the ends of the polypeptide sequence, they are predicted to be located in close proximity to each other in the polypeptide structure (see FIG. 4a). The ribbon structure in FIG. 4b showed that the PR-9 insertion between Ile-8 and Pro-9 is predicted to create a short alpha helical structure, located just prior to the beginning of the β1 strand. One effect of the insertion is the re-orientation of the Pro-9 to the backside of the polypeptide face (see FIG. 4a). The PR-55 insertion, located between Ala-54 and His-55, is predicted to create a kink within the loop structure between β4 and β5. The result is the disappearance of Ala-54 from the surface of the polypeptide (see FIG. 4a). And finally, the PR-100 mutation, between Val-99 and Cys-100, is predicted to result in the early termination of the β7 strand. The space-filling model predicts that the net effect of the insertion is a separation of the valine and cysteine residues. Together, the modeling information shows that the PR insertions are located on an exposed region of SRCR5. The PR insertions are predicted to have a specific and localized effect on SRCR5 structure. The PR-9 and PR-100 mutations, even though located near the ends of the peptide sequence are located in close proximity to each other within the SRCR5 three dimensional protein structure.

The PRRSV-resistant properties of the PR-9, PR-55, and PR-100 mutations were further investigated by comparing titration end-points and growth curves for HEK cells transfected with the different mutants. The results for three independent titration experiments are presented in Table 3. HEK cells transfected with the wild type CD163 plasmid served as a positive control. The results for three independent experiments showed that the initial mean percentage of infected WT CD163 cells was 59.3 +/−3.6, with a titration end-point of 10-3 for all three experiments. In contrast, the infection of HEK cells expressing PR-9, PR-55 and PR-100 CD163 constructs showed only a few infected cells. The mean percent infection ranged between 0.8 and 3.0%. The titration end-point for PR-9 and PR-100 was $10^{-2}$. The titration end-point for PR-55 was $10^{-1}$. These results show that the mutations lessen the ability of PRRSV to interact with CD163. Furthermore, the data showed that the PR-55 mutation produced the greatest negative effect on PRRSV infection.

The results for the titration experiments were supported by growth curves (see FIG. 5). For the growth curve experiment, samples from transfected HEK cells were collected every 12 hrs. After washing, the residual virus remaining in the well after infection was 4 $\log_{10}$ $TCID_{50}$/ml for all constructs. The concentration of virus in the HEK cells transfected with the wild type CD163 peaked at 7 $\log_{10}$ $TCID_{50}$/ml, which represents a 3 log increase in virus concentration. In contrast, virus infection of the PR mutants showed no increase in virus concentration over time. Furthermore, virus concentrations continued to decay over time, reaching undetectable levels by 36 hrs. The results indicate that expression of the mutant CD163 proteins resulted in no net increase in virus infection, thus confirming the high resistant properties of PR-9, PR-55 and PR-100.

As illustrated in FIG. 3, SRCR5 is predicted to possess four disulfide bonds formed by the eight cysteine residues located at amino acid positions 10, 26, 39, 44, 70, 80, 90 and 100. For these experiments, individual disulfide bonds were removed by substituting one of the partner cysteines with an alanine. Alanine to cysteines substitutions were made for C1, C3, C5 and C7. For C1, C3 and C5, the codons for two existing proline-arginine dipeptides, located at positions 1 and 84 of SRCR5, were changed to SacII sites. The CD163-EGFP plasmid was cut with SacII and the intervening DNA sequence replaced with a synthesized fragment (IDT, Inc.) possessing SacII restriction sites on the ends. The proper orientation of the cDNA insert was confirmed by DNA sequencing. Since C7 is located near the PR-84, the alanine substitution was made by amplifying the plasmid using a unique primer pair possessing SacII restriction sites and the codon for the alanine substitution (see Table 1). The results showed that all alanine mutations conferred resistance to transfected HEK cells infected with PRRSV-RFP. The reduction in infection (percent infected cells) was greater than 20 fold.

In some forms of the present disclosure, exon 13 of CD163 is disrupted by mutation to the sequence thereof. Preferably, the mutation is in frame such that the mutation's effects are only to exon 13. In one embodiment, the mutation is a deletion of at least a portion of exon 13. Such a portion can encompass just a single codon encoding for a single amino acid. In other embodiments, such a portion can encompass 2, 3, 4, 5, 6, 7, 8, 9, 10, 11, 12, 13, 14, 15, or 16 amino acids. In other embodiments, the mutation includes a deletion, as described above, accompanied with an insertion of the same, or a different number of codons for the same or a different number of amino acids. Such a deletion and accompanying insertion can be termed a "substitution". Thus, mutations which incorporate a deletion also confer resistance to infection by PRRSV, as described herein.

In some forms of the present disclosure, peptides are inserted into CD163 as described above. In other forms, dipeptides (other than those disclosed above), tripeptides, tetrapeptides, or other oligopeptides are inserted into CD163, as described above. Preferably, the insertion is in-frame and utilizes the least number of peptides as needed to disrupt the secondary protein structure of CD163 such that it is more resistant to (in comparison to CD163 that does not have an insertion therein) or is no longer permissive to PRRSV infection. The restriction site can also be placed in a different reading frame, creating a different effect on primary and secondary protein structure, such as the insertion of an alanine. In some preferred forms, the peptide or oligopeptide includes a charged amino acid. Preferably, the charged amino acid is selected from the group consisting of arginine, lysine, aspartic acid, and glutamic acid. In other preferred forms the peptides or oligopeptide includes a hydrophobic amino acid. In some particularly preferred forms of the disclosure, a charged amino acid is combined with at least one hydrophobic amino acid. Preferably, the hydrophobic amino acid is selected from the group consisting of alanine, isoleucine, leucine, phenylalanine, valine, proline, and glycine. When oligopeptides larger than dipeptides are utilized, use of one or more charged amino acids or one or more hydrophobic amino acids is preferred. In other preferred forms, one or more charged amino acids and one or more hydrophobic amino acids are utilized. The remaining amino acids can be any natural or non-natural amino acid.

In other preferred forms, the location for insertion of peptides or oligopeptides is selected based on the proximity to beta sheets and/or alpha helices. In some forms, the insertion site is within 1, 2, 3, 4, 5, 6, 7, 8, 9, or 10 amino acids of the beginning of the beta sheet or alpha helix. This can be either prior to the beginning of the beta sheet or alpha helix, within or after the sequence of the beta sheet or alpha helix. In other forms, the insertion site is within 1, 2, 3, 4, 5, 6, 7, 8, 9, or 10 amino acids of the beginning or end of a disulfide bond.

The term "resistant" refers to a comparison of the permissiveness of cells to PRRSV infection. A cell that is more resistant to PRRSV infection allows less PRRSV infection compared to an unmodified cell. Preferably, cells modified in accordance with the present disclosure are 5% more resistant, preferably 10%, 15%, 20%, 25%, 30%, 35%, 40%, 45%, 50%, 55%, 60%, 65%, 70%, 75%, 80%, 85%, 90%, 95%, 96%, 97%, 98%, 99%, or more resistant to PRRSV infection than unmodified cells. Similarly, a group of cells modified as described herein is more resistant when a fewer number of cells of the group allow infection with PRRSV compared to an unmodified group of cells. Preferably, a group of cells modified in accordance with the present disclosure are 5% more resistant, preferably 10%, 15%, 20%, 25%, 30%, 35%, 40%, 45%, 50%, 55%, 60%, 65%, 70%, 75%, 80%, 85%, 90%, 95%, 96%, 97%, 98%, 99%, or more resistant to PRRSV infection than a group of unmodified cells.

Conversely, the term "reducing the susceptibility" refers to a comparison of the susceptibility of cells to PRRSV infection. A cell that is less susceptible to PRRSV infection allows less PRRSV infection compared to an unmodified cell. Preferably, cells modified in accordance with the present disclosure are 5% less susceptible, preferably 10%, 15%, 20%, 25%, 30%, 35%, 40%, 45%, 50%, 55%, 60%, 65%, 70%, 75%, 80%, 85%, 90%, 95%, 96%, 97%, 98%, 99%, or less susceptible to PRRSV infection than unmodified cells. Similarly, a group of cells modified as described herein is less susceptible when a fewer number of cells of the group allow infection with PRRSV compared to an unmodified group of cells. Preferably, a group of cells modified in accordance with the present disclosure are 5% less susceptible, preferably 10%, 15%, 20%, 25%, 30%, 35%, 40%, 45%, 50%, 55%, 60%, 65%, 70%, 75%, 80%, 85%, 90%, 95%, 96%, 97%, 98%, 99%, or less susceptible to PRRSV infection than a group of unmodified cells.

As noted above, in one preferred form, the peptide or oligopeptide also functions as a detectable sequence that confirms the presence of the modification. The presence of a SacII restriction site, to insert a dipeptide or other peptide sequence not resulting in an amino acid change, also functions as a confirmatory diagnostic. When the restriction site is detected, one of skill in the art knows that the modification is present. One of skill in the art will be able to select other such peptides and oligopeptides that function in a similar fashion. Alternatively, the peptides or oligopeptides utilized in accordance with this disclosure can be tagged or coupled with a detectable moiety that confirms the presence of the modification.

Another aspect of the present disclosure is providing a method of reducing the susceptibility of a cell to infection by PRRSV comprising the steps of introducing a modification to the cell's genome, wherein the reduction of susceptibility is in comparison to a cell that has not been modified, and wherein the modification is selected from the group consisting of: a) deleting a portion of exon 13; b) deleting at least one of the SRCR8 and SRCR9 domains; c) inserting coding sequences into the genome; d) deleting at least one disulfide bond; e) deleting at least a portion of, or amino acid substitution within, the SRCR4-5 interdomain sequence; f) deleting at least a portion of the SRCR5 domain; g) deleting at least a portion of the PSTII region; h) substituting a coding sequence in the genome; and i) any combination thereof. In some preferred forms, the modification of exon 13 includes the deletion of at least 10 amino acids. In other preferred forms, the modification of exon 13 includes the complete deletion of exon 13. In some preferred forms, the modification of deleting at least one of the SRCR8 and SRCR9 domains further includes the insertion of proline-arginine residues into the deleted domains. In still other preferred forms, the modification of inserting coding sequences into the genome includes inserting proline-arginine residues. In still other preferred forms, these coding sequences are inserted into the SRCR domain 5. In some preferred forms, the proline arginine residues are inserted after the $8^{th}$ or the $54^{th}$, or the $99^{th}$ amino acid in SRCR5. In some forms of deleting at least one disulfide bond, the modification includes deleting a plurality of disulfide bonds. In some preferred forms, the cysteine of at least one of the deleted disulfide bonds is replaced with alanine. In some preferred forms, the disulfide bonds are located in the SRCR5 region. Preferably, a cell with modified genome as described above is at least 50% less susceptible than an unmodified cell.

BRIEF DESCRIPTION OF THE DRAWINGS

FIG. 1A illustrates the deletion mutants used in the transfection of HEK293T cells wherein ovals and squares identify the SRCR and PST domains, respectively;

FIG. 1B is a photograph of the Western blots results using anti-GFP antibody for the detection of the CD163-EGFP fusion protein;

FIG. 1C is a schematic of the result for PRRSV infection of transfected cells wherein (+++), similar to results for wild type CD163 including numerous large clusters of infected cells; (++), several small clusters of infected cells; (+), multiple single infected cells, but no clusters; (+/−), a few scattered infected cells; (−), no detectable infected cells.

FIG. 2A illustrates constructs for which peptide sequences are shown in FIG. 2B.

FIG. 2B illustrates the peptide sequences for the constructs shown in FIG. 2A, (SEQ ID NO. 21, 22, 23 and 24), respectively, wherein the peptide sequence shown in bold letters (SEQ ID NO. 57), flanked by SEQ ID NOs. 61 and 62 is the region covered by the PSTII domain. SEQ ID NO. 78 represents the Exon 13 deletion. The infection results are described in FIG. 2A.

FIG. 2C is a graph illustrating the surface expression of CD163 for the same constructs shown in FIGS. 2A-B.

DETAILED DESCRIPTION

Figure 3:
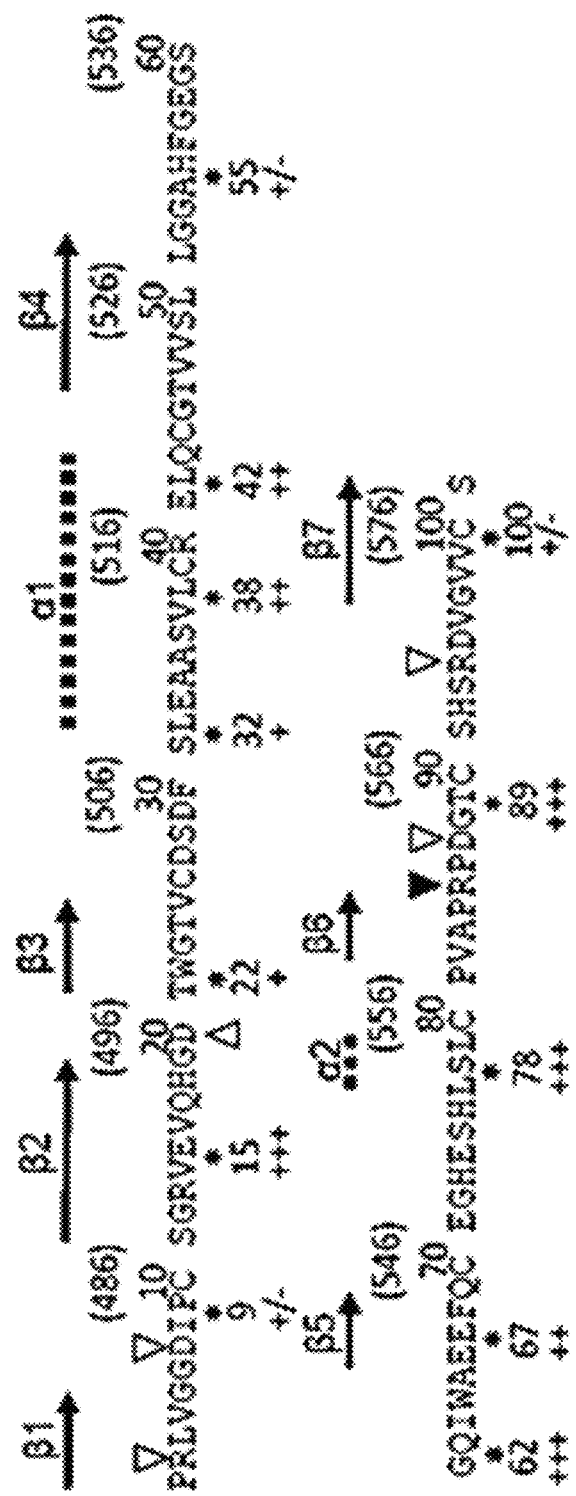
FIG. 3 is an illustration of SEQ ID NO. 58 showing the location of PR insertions in SRCR5 of porcine CD163 wherein the SRCR5 peptide sequence is from GenBank No. AJ311716. The peptide sequence position number is above the sequence with the CD163 coordinates in parentheses. The arrows show the location and direction of beta sheets and the dotted lines show the location of alpha helices. The asterisks show the location of the proline-arginine insertions. Below each construct is the result for infection of transfected HEK293T cells, which is also described in the description for FIG. 1C.

The following description is merely exemplary in nature and is in no way intended to limit the present teachings, application, of uses. Thus, variations that do not depart from the gist of that which is described are intended to be within the scope of the teachings. Such variations are not to be regarded as a departure from the spirit and scope of the teachings.

Example 1

Materials and Methods

Virus and cells. The type 2 PRRSV was originally derived from an infectious clone that expressed a red fluorescent protein (RFP). Virus was propagated on MARC-145 cells in media containing 7% FBS, Pen-Strep (80 U/ml and 80 μg/ml, respectively), 3 μg/ml Fungizone, and 25 mM HEPES. For virus titration, the samples were serially diluted 1:10 and propagated on MARC-145 cells. Dilutions were performed in quadruplicate. The titration end-point was determined as the last well showing CPE. The logo 50% tissue culture infectious dose ($TCID_{50}$)/ml was calculated according to the method of Reed and Muench.

Construction of CD163 deletion mutants. The backbone for the preparation of the mutated CD163 constructs was a porcine CD163 cDNA (GenBank Acc No. EU016226) cloned into a pcDNA3.1-EGFP expression vector. The truncated CD163 cDNA fragments were prepared by PCR amplification of the pcDNA template using the GoTaqGreen® Master Mix (Promega) according to manufacturer's instructions. PCR conditions included 95° C. for 2 min, followed by 30 cycles of 94° C. for 30 s, 65° C. for 30 s, and 72° C. for 2 min, and a final extension at 72° ° C. for 10 min. The PCR primers are listed in Table 1. The PCR products were cloned into pCR 2.1-TOPO® vector (Invitrogen) and transformed into One Shot® TOP10 chemically competent *E. coli* cells (Invitrogen). The purified plasmids were double-digested with KpnI and Xbal and cloned into the KpnI-Xbal sites of the pcDNA3.1-EGFP vector. Plasmids were transfected into HEK cells using FuGENE® HD reagent (Promega) according to manufacturer's instructions and viewed for the presence of EGFP expression under a fluorescence microscope. The resulting N-terminally truncated proteins are illustrated in FIG. 1A (constructs B through H).

Constructs that possessed deletion domains from the C-terminal end of CD163 incorporated primers with PacI restriction sites, which are listed in Table 1. Deletions were made using a long PCR protocol designed to amplify the desired CD163 fragment along with the entire pcDNA3.1-EGFP plasmid. PCR amplification was performed using LongAmp® Taq DNA Polymerase (New England Biolabs Inc). PCR conditions included 94° C. for 30 seconds, followed by 30 cycles of 94° C. for 30 seconds, 65° C. for 1 minute, and 65° C. for 8 minutes, followed by a final extension at 65° C. for 10 minutes. The PCR products were cut with PacI and the plasmid re-circularized by ligation with Anza™ T4 DNA Ligase Master Mix (Invitrogen), and then transfected into HEK cells. The resulting CD163 deletion constructs retained intact transmembrane and cytoplasmic domains along with an added PacI site (see FIG. 1—constructs I through O). The CD163 PSTII partial and complete deletion constructs incorporated primers that possessed SacII restriction sites. The SacII sites were placed in a reading frame to code for alanines.

Insertion mutagenesis of SRCR5. Proline-arginine (PR) insertions into SRCR5 were achieved by inserting SacII sites into the CD163 cDNA plasmid. The method for insertion of SacII sites was the same as described for the preparation of the C-terminal deletion mutants. The intact pcDNA3.1 CD163-EGFP was used as a template and the entire plasmid amplified using LongAmp® Taq DNA Polymerase and the same amplification conditions described above for the C-terminal truncations. The primers used for amplification are listed in Table 2.

Western blot analysis. Cell monolayers on a 24-well plate were washed once with cold PBS followed by the addition of 300 µl NP-40 lysis buffer to each well (Invitrogen). Cells were removed with a cell scraper and transferred to a microcentrifuge tube. After a 30 minute incubation on ice under constant agitation, the supernatant was removed and proteins separated on a 10% SDS-PAGE gel. Proteins were transferred to a 0.45 µm PVDF membrane: the SDS-PAGE gel was rinsed in PBS-Tween 20 (PBST) and the PVDF membrane was submerged in methanol for membrane activation, followed by rinsing in double-distilled water for 10 minutes. Prior to assembly, the gel, filter paper (0.83 mm) and PVDF membrane were soaked for 20 minutes in 1× transfer buffer (0.03 M glycine, 0.04 M tris base, 0.04% SDS, double-distilled water and 20% methanol). The blot apparatus was assembled and electrophoretic transfer performed on a Mini Trans-Blot® Electrophoretic Transfer Cell (BIO-RAD) following the manufacturer's instructions. After transfer, the membrane was blocked overnight in PBS with 5% non-fat dry milk (PBS-NFDM) at 4° C. The CD163-EGFP fusion proteins were detected with horseradish peroxidase (HRP)-conjugated goat anti-GFP antibody (R&D Systems), diluted 1:1000 in PBS-NFDM for 1 hour at room temperature. Peroxidase activity was visualized using a CN/DAB Substrate Kit (Thermo Scientific Pierce) according to the kit instructions. The peroxidase reaction was stopped by rinsing the membrane with double-distilled water.

Flow cytometry for surface expression of CD163. At 72 hours after transfection with CD163 plasmids, HEK cells were washed twice with PBS and detached with TrypLE™ Express (Thermofisher Scientific) according to manufacturer's instructions. Cells were adjusted to a concentration of approximately $2\times10^7$/ml in PBS with 5% mouse serum (PBS-MS) and 100 µl placed in 12 mm×75 mm polystyrene flow cytometry tubes. Cells were pelleted by centrifugation and re-suspended in 100 µl of mouse anti-porcine CD163 mAb at a concentration of 10 µg/ml in PBS-MS (Clone: 2A10/11, AbD Serotec). After a 30 minute incubation on ice, the cells were washed twice with PBS containing 1% fetal bovine serum (FBS; MIDSCI Co.) and incubated with 1:100 dilution of rabbit anti-mouse conjugated with allophycocyanin (APC; 0.5 mg/ml, Jackson ImmunoResearch), for 30 minutes on ice. Samples were washed twice with PBS containing 1% FBS and brought to a final volume of 300-500 µl and analyzed on the BD LSR Fortessa X-20 Flow Cytometer (BD Biosciences) with FCS Express 5 software (De Novo Software). A minimum of 10,000 cells were analyzed for each sample.

Computer prediction of PR insertions in SRCR5. Coordinates for the CD163 SRCR5 peptide sequence were accessed through the RCSB Protein Data Bank (PDB code 5JFB; deposited by Ma et al., 2017). The structural predictions for the proline-arginine (PR) insertion mutations were generated using the PyMOL molecular graphics and modeling system. The I-TASSER V5.1 simulator was used for the refinement of the predicted conformational changes. A C-score value was used to determine the accuracy of the simulation. C-scores between 1.0 and 2.0 were considered accurate. For simulations that gave multiple model structures, the prediction with the greatest C-score value was chosen. The generated structures were loaded into the open source molecular visual program, UCSF Chimera, for analysis.

Figure 6:
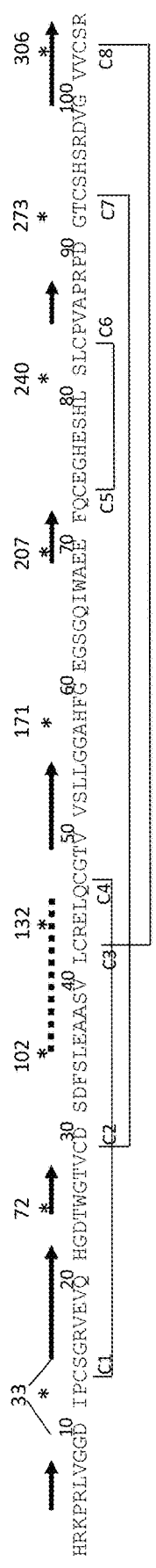
FIG. 6 is a schematic depicting the location of SacII insertion sites in domain 5 of porcine CD163 (unmodified CD163) (SEQ ID NO. 60) in comparison to the location of the disulfide bonds.

Removal of disulfide bonds in SRCR5. As illustrated in FIGS. 3 and 6, there are eight cysteines that form four disulfide bonds in SRCR5 (Ma et al., 2017). Individual disulfide bonds were interrupted by deleting one of the participating cysteines. Unique restriction sites were placed in the pcDNA3.1 CD163-EGFP plasmid by changing the codons for two existing proline-arginine dipeptides, located at positions 1 and 84 of SRCR5, to SacII restriction sites. The nucleotide changes did not affect the SRCR5 polypeptide sequence. The CD163-EGFP plasmid was cut with SacII and intervening DNA sequence replaced with synthesized fragments (IDT) possessing SacII sites on the ends. Four DNA fragments were synthesized, which included cysteine to alanine substitutions at C1, C3, C5 or C7 (see FIG. 6). The final CD163-EGFP plasmids were transfected into HEK cells and infected with P129-RFP.

Results

Infection of HEK cells transfected with CD163 domain deletion mutants. The CD163-EGFP deletion constructs transfected into HEK cells are described in FIG. 1A. All constructs showed EGFP fluorescence within 24 hrs after transfection of plasmids. Western blots stained with anti-GFP antibody confirmed that each construct migrated according to the predicted size (FIG. 1B). HEK cells transfected with the full-length CD163-EGFP fusion plasmid, Construct A, served as a positive control for infection with the PRRSV-RFP virus. A plasmid expressing a soluble form of CD163-EGFP, Construct H, was included as a negative infection control. The N-terminal truncation mutants are identified as constructs B-G. Constructs A-D, which contained SRCR5 were positive for infection. The remaining N-terminal deletion mutants, constructs E-G, which lacked SRCR5, were negative for infection. The results for the C-terminal deletions lacking PSTII, constructs I through K, were all negative for infection, including the constructs J and K, which retained the SRCR5 domain. Constructs N and O, which were identical to J and K, except for the addition of the PSTII domain were positive for infection. When taken together, all of the constructs in FIG. 1 lacking SRCR5 or PSTII were negative for infection.

The 16 amino acid PSTII domain can be divided into two regions. The exon 14 portion consists of the four amino acids, GRSS (SEQ ID NO. 55) (see FIG. 2B). The remainder of exon 14 includes the transmembrane domain and a portion of the cytoplasmic tail. The substitution of GRSS (SEQ ID NO. 21-22) with three alanines (Construct P) resulted in only a small reduction in infection. The removal of the remaining 12 amino acids within PSTII blocked infection. The results in FIG. 2C showed that all constructs were expressed on the surface of transfected HEK cells. Therefore, the deletion of the region of CD163 encoded by exon 13 is sufficient to prevent infection. When taken together, the results from the experiments in FIGS. 1 and 2 demonstrate that type 1 and type 2 PRRSV possess similar requirements for SRCR5 and PSTII domains.

The effect of PR insertions in SRCR5 on PRRSV infection. The approach for the characterization of polypeptide sequences within SRCR5 involved in the recognition of CD163 incorporated the disruption of primary and/or secondary polypeptide structure through the insertion of single proline-arginine (PR) dipeptides. SRCR5 already possesses two naturally occurring PR dipeptides, located at positions 1 and 84 (see FIG. 3). The primers for inserting the SacI sites, listed in Table 2, were designed to place a PR dipeptide at about every 10 amino acids along the SRCR5 polypeptide sequence (see FIG. 3). The results after infection with PRRSV-RFP identified three mutations, PR-9, PR-55, and PR-100, which produced the greatest reduction of RFP-positive cells. In addition, the deletion of, or amino acid substitution within, the SRCR4-5 interdomain peptide sequence, AHRK, also affected virus infection.

Figure 4A:
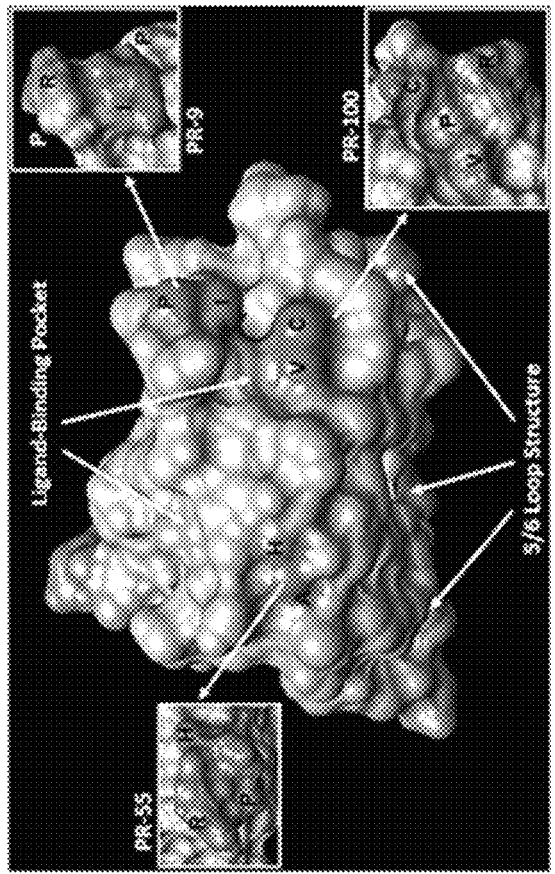
FIG. 4A is an illustration of the location of PR insertion mutations in SRCR5. This figure shows the location of the PR insertion mutations (red areas) on the surface of the space filling model. The inserted PR dipeptides are shown in green.
Figure 4B:
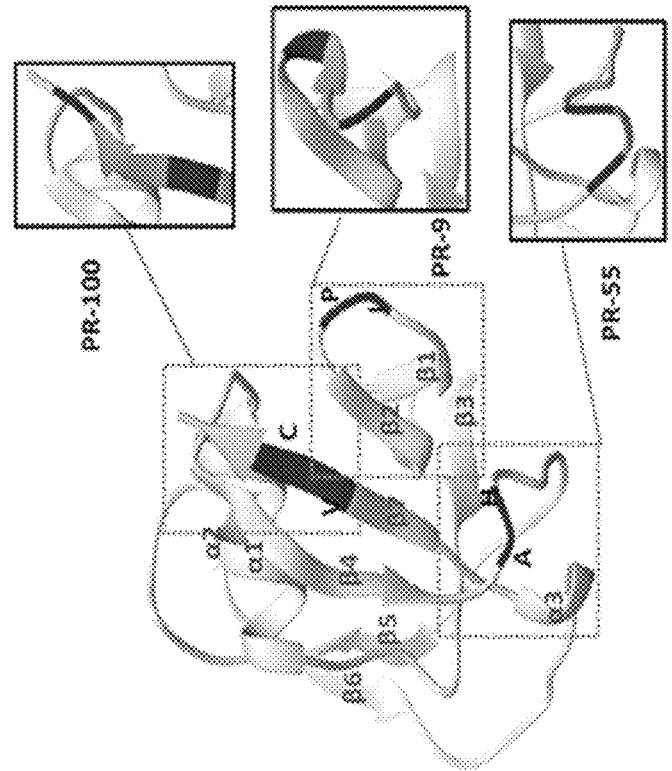
FIG. 4B shows the ribbon structure of SRCR5 and the effect of the individual PR mutations on the protein structure. The structures are based on the X-ray crystallography data deposited in RCSB Protein Data Bank (PDB code 5JFB) and viewed using UCSF Chimera.

The predicted locations of the PR-9, PR-55 and PR-100 mutations on the surface of the SRCR5 structure are shown in FIG. 4A. A space-filling model showed that the three mutations were located on a single face of the SRCR5 polypeptide, in close proximity to the Ligand-binding pocket (LBP) and the loop 5-6 region previously described by Van Gorp et al., 2010 and Graversen et al., 2002. Even though the PR-9 and PR-100 mutations are located at the ends of the polypeptide sequence, they are predicted to be in close proximity to each other in the polypeptide structure (see FIG. 4A). The ribbon structure in FIG. 4B showed that the PR-9 insertion between Ile-8 and Pro-9 is predicted to create a short alpha helical structure, located just prior to the beginning of the β1 strand. One effect of the insertion is the re-orientation of the Pro-9 to the backside of the polypeptide face (see FIG. 4A). The PR-55 insertion, located between Ala-54 and His-55, is predicted to create a kink within the loop structure between β4 and β5. The result is the disappearance of Ala-54 from the surface of the polypeptide (see FIG. 4A). And finally, the PR-100 mutation, between Val-99 and Cys-100, is predicted to result in the early termination of the β7 strand. The space-filling model predicts that the net effect of the insertion is a separation of the valine and cysteine residues. Together, these data show that the PR insertions are predicted to produce only small localized changes in the overall SRCR5 structure.

A more careful analysis of the effect of the PR-9, PR-55 and PR-100 insertions on infection was performed by comparing titration end-points and growth curves for HEK cells transfected with the different mutants. The results for three independent titration experiments are presented in Table 3. HEK cells transfected with the wild type CD163 plasmid served as a positive control. The results for three independent experiments showed that the initial mean percentage of infected WT CD163 cells was 59.3 +/−3.6, with a titration end-point of $10^{-3}$ for all three experiments. In contrast, the infection of HEK cells expressing PR-9, PR-55 and PR-100 CD163 constructs showed only a few infected cells. The mean percent infection ranged between 0.8 and 3.0%. The titration end-point for PR-9 and PR-100 was $10^{-2}$. The titration endpoint for PR-55 was $10^{-1}$.

TABLE 3

Percent infection of HEK293T cells transfected with different PR dipeptide insertion constructs*

|  | Exp. 1 | Exp. 2 | Exp. 3 | Mean ± SD |
|---|---|---|---|---|
| $10^{-1}$ Dilution of Virus | | | | |
| WT | 55.3 | 62.3 | 60.4 | 59.3 ± 3.6 |
| PR-9 | 2.1 | 3.0 | 1.6 | 2.2 ± 0.7 |
| PR-55 | 1.7 | 1.6 | 1.4 | 1.6 ± 0.2 |
| PR-100 | 0.8 | 1.1 | 1.2 | 1.0 ± 0.2 |
| $10^{-2}$ Dilution of Virus | | | | |
| WT | 28.5 | 28.5 | 30.6 | 29.2 ± 1.2 |
| PR-9 | 0.7 | 1.0 | 0.6 | 0.8 ± .2 |
| PR-55 | 0.0 | 0.0 | 0.0 | 0 |
| PR-100 | 0.4 | 0.5 | 0.4 | .4 ± 0.1 |
| $10^{-3}$ Dilution of Virus | | | | |
| WT | 3.2 | 4.5 | 6.6 | 4.8 ± 1.7 |
| PR-55 | 0 | 0 | 0 | 0 |
| PR-100 | 0 | 0 | 0 | 0 |
| $10^{-4}$ Dilution of Virus | | | | |
| WT | 0 | 1.3 | 1.4 | 1.4 |
| $10^{-5}$ Dilution of Virus | | | | |
| WT | 0 | 0 | 0 | 0 |

*Cells were infected with different dilutions of PRRSV-RFP virus (starting concentrations = 6.5 $Log_{10}TCID_{50}$/ml). Results are shown as percent infection of CD163-positive HEK293T cells at 72 hrs after infection. Each experiment was performed on a single 24 well plate. Transfection efficiency, as determined by the percentage of green fluorescent cells for the CD163-EGFP plasmid constructs was between 60 and 70% (data not shown)

Figure 5:
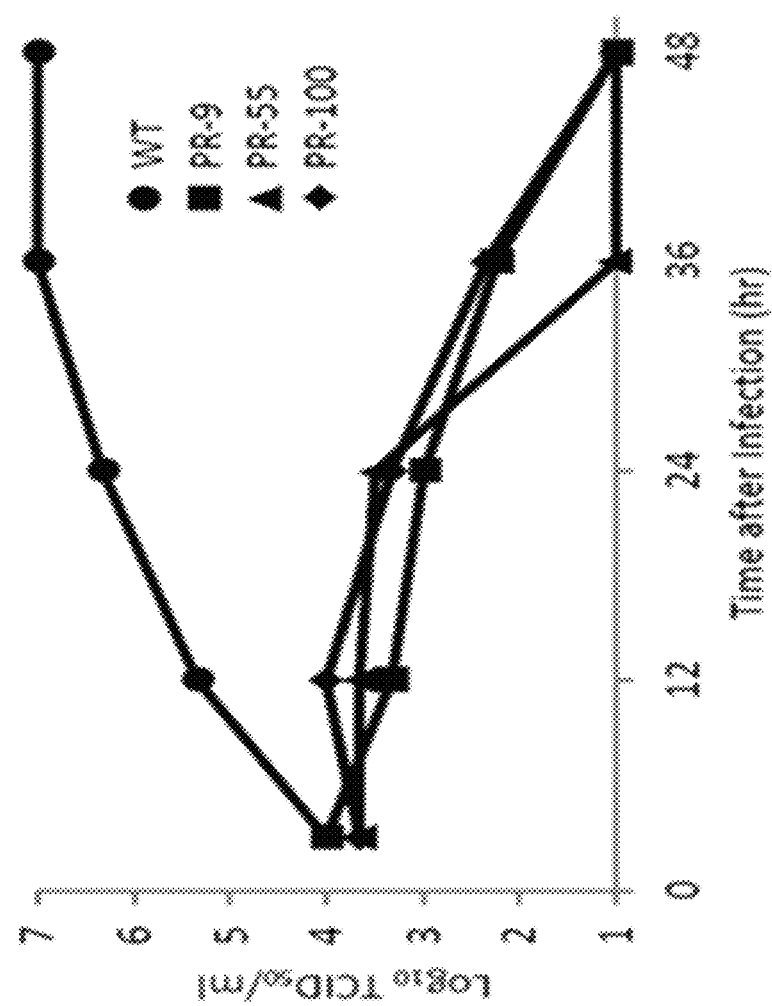
FIG. 5 is a graph of the growth curves for HEK293T cells transfected with wild type and mutant CD163 constructs. HEK cells were transfected with different mutant constructs and, after 24 hrs, were infected with PRRSV-RFP. Two hours post-infection, the cells were washed and media was collected every 12 hrs. The $TCID_{50}$ was calculated by titration of viruses on MARC-145 cells. Results are shown for a single experiment.

The results for the titration experiments were supported by growth curves (see FIG. 5). For the growth curve experiment, samples from transfected HEK cells were collected every 12 hrs. After washing, the residual virus remaining in the well after infection was 4 $log_{10}$ $TCID_{50}$/ml for all constructs. The concentration of virus in the HEK cells transfected with the wild type CD163 peaked at 7 $log_{10}$ $TCID_{50}$/ml, which represents a 3 log increase in virus concentration. In contrast, virus infection of the PR mutants showed no increase in virus concentration over time. Furthermore, virus concentrations continued to decay over time, reaching undetectable levels by 36 hrs. These data show that the PR-9, 55, and 100 mutations in SRCR5 of CD163 severely impair the ability of PRRSV to infect cells.

The effects of modifications in the SRCR4-5 interdomain peptide sequence, AHRK, on infection. The peptide sequence, alanine-histidine-arginine-lysine (AHRK) (SEQ ID NO. 64) is located between SRCR4 (KITCS (SEQ ID NO. 63)) and SRCR5 (PRLVG (SEQ ID NO. 76)) domains. Table 3 shows the effect of making deletions, insertions and amino acid substitutions in the AHRK (SEQ ID NO. 64) peptide sequence. All constructs shown in Table 4 possess the intact CD163, with on mutation within the AHRK (SEQ ID NO. 64) peptide sequence. For example, CD163 Construct No. 2, which possesses a complete deletion of AHRK (SEQ ID NO. 64) produced a dramatic reduction in infection. The substitution of AHRK (SEQ ID NO. 64) with AAAA (SEQ ID NO. 65) (Construct No. 3) retained the four amino acids, but still produced a reduction in infection. Further substitution of AHRK (SEQ ID NO. 64) with AAAK (SEQ ID NO. 66) (Construct No. 4), AARA (SEQ ID NO. 68) (Construct No. 6), or AKKK (SEQ ID NO. 72) (Construct No. 10), resulted in reduced infection. Examples of how the insertion of an amino acid can affect infection are found in the results for constructs no. 12 and 13. Together, these results demonstrate that amino acid deletions, insertions and substitutions within the SRCR4-5 interdomain region affect the ability of CD163 to function as a receptor for PRRSV.

TABLE 4

Peptide sequence modifications in the SRCR4-5 that affect infection
Peptide Sequence

| No. | SRCR4 | SEQ ID NO. | Inter-domain | SEQ ID NO. | SRCR5 | SEQ ID NO. | Infection* |
|---|---|---|---|---|---|---|---|
| 1 | KITCS | 63 | AHRK | 64 | PRLVG | 76 | +++ |
| 2 | ..... | | - - - - | | ..... | | +/- |
| 3 | ..... | | .AAA | 65 | ..... | | +/- |
| 4 | ..... | | .AA. | 66 | ..... | | +/- |
| 5 | ..... | | ..AA | 67 | ..... | | +++ |
| 6 | ..... | | .A.A | 68 | ..... | | +/- |
| 7 | ..... | | .A.. | 69 | ..... | | +++ |
| 8 | ..... | | ...R | 70 | ..... | | +++ |
| 9 | ..... | | ..K. | 71 | ..... | | ++ |
| 10 | ..... | | .KK. | 72 | ..... | | +/- |
| 11 | ..... | | D... | 73 | ..... | | +++ |
| 12 | ..... | | AHRAK | 74 | ..... | | +/- |
| 13 | ..... | | AHARK | 75 | ..... | | + |

*Key:
++++, infection of multiple cells with foci containing clusters of infected cells;
+++, fewer number of infected cells, but still possessing foci containing clusters of infected cells;
++, several single cells infected with virus;
+ a small number of cells showing infection;
+/- only one or two infected cells in the well.

The effect of the removal of disulfide bonds in SRCR5 of CD163 on infection. As illustrated in FIG. 6, SRCR5 is predicted to possess four disulfide bonds formed by the eight cysteine residues located at amino acid positions 10, 26, 39, 44, 70, 80, 90 and 100. For these experiments, SacII sites were inserted into the SRCR5 region of CD163 in such as manner as to not affect the underlying peptide sequences. DNA segments were synthesized that possessed SacII sites of the DNA strand on the ends along with cysteine to alanine substitutions at positions, 10, 39, 70 or 90. The alanine substitutions were designed to interrupt each disulfide bond, one at a time. The results showed that all alanine mutations conferred resistance to transfected HEK cells infected with PRRS-RFP. The reduction in infection (percent infected cells) was greater than 20 fold. (See Table 5)

TABLE 5

Effect of disulfide bonds on type 2 PRRSV infection

| Mutation | Disulfide Bond | %* |
|---|---|---|
| None | NA | 61.2 |
| Cys-10 | C10-C44 | 0.8 |
| Cys-26 | C26-90 | 1.0 |
| Cys-39 | C39-C100 | 1.2 |
| Cys-70 | C70-80 | 1.3 |

*Percent infection calculated as the number of red cells (infected) divided by the number of green cells (CD163 expressing) at the 72 hrs after infection with PRRSV-REP. The percentage of EGFP-expressing cells was between 60-70 for all constructs.

DISCUSSION

The genetic modification of pigs that lack CD163 expression on macrophages are completely resistant to infection with PRRSV-1 and PRRSV-2. For example, CD163-modified pigs that possess a substitution of SRCR5 with a human CD163-like SRCR8 homolog domain are resistant to infection with PRRSV-1 isolates but retain the capacity to be productively infected with PRRSV-isolates. To better understand the difference in how PRRSV-1 and PRRSV-2 viruses recognized PRRSV, experiments were performed to determine the effect of domain deletions in CD163 on transfected HEK cells infected with a PRRSV-2 virus. The results showed that deletions in SRCR5 or PSTII conferred resistance to infection with PRRSV-RFP. The deletion of other domains, such as SRCR7, 8 and 9, had a lesser effect on infection. In terms of the individual domains involved in PRRSV infection, there appears to be no significant difference between PRRSV-1 and PRRSV-2 viruses. The requirement for SRCR5 was recently confirmed by demonstrating that macrophages from genetically modified pigs possessing a deletion in SRCR5 are resistant to both PRRSV-1 and PRRSV-2 viruses. Therefore, these data indicate that the difference between PRRSV-1 and PRRSV-2 viruses in the recognition of CD163 locates within SRCR5.

The purpose of this study was to investigate the regions within SRCR5 and PSTII that are important to recognition of PRRSV. The goal is to construct CD163 receptors that are resistant to PRRSV, while retaining overall CD163 function. The approach for identifying regions in SRCR5 involved in recognition by PRRSV was the insertion of single PR dipeptides along the entire SRCR5 peptide sequence. Three PR mutations, inserted after amino acids 8 (PR-9), 54 (PR-55), or 99 (PR-100) of the SRCR5 sequence produced the greatest impact on the infection of CD163-transfected HEK cells (see Table 3). Reduced infection was supported by the structural changes imposed on SRCR5 by each mutation. Even though the mechanism for reduced infection is not known, one possibility is that the interruption of the primary and/or secondary protein structure is sufficient to interrupt the interaction between SRCR5 and corresponding amino acids on a corresponding PRRSV protein. Very little is known regarding the PRRSV proteins that form interactions with CD163. The fact that both PSTII and SRCR5 are spatially separated from each other suggests that multiple envelope proteins form multiple contacts with CD163. The best available model for the interaction between CD163 and PRRSV involves the heterotrimer formed by GP2, GP3 and GP4. In addition, the surface of the virion is populated by GP5-M homodimers. Additional viral glycoproteins, such as GP3 and the GP5-M heterodimer, may further stabilize the virus-receptor complex. After infection of transfected HEK cells possessing the PR-9, PR-55 and PR-100 mutations, a small number of infected cells remained. The persistence of a similar background level for all three mutants indicates that more than one region in SRCR5 participates in PRRSV infection.

What is claimed is:

1. A method of reducing susceptibility of a cell to infection by porcine reproductive and respiratory syndrome virus (PRRSV) comprising introducing a modification to the cell's genome, wherein the reducing susceptibility is in comparison to a cell that has not been modified, and wherein the modification comprise:
   disrupting at least a portion of exon 13 sequence of CD163, wherein the modification does not comprise a disruption of exon 14 sequence of CD163, and wherein the modification is sufficient for the reducing susceptibility.

2. The method of claim 1, wherein the modification results in deletion of at least 10 amino acids of a CD163 protein.

3. The method of claim 1, wherein the modification comprises a complete deletion of the exon 13 sequence.

4. The method of claim 1, wherein the cell with the modification is at least 50% less susceptible to the infection by PRRSV than the cell that has not been modified.

* * * * *

SEQUENCE LISTING

<160> NUMBER OF SEQ ID NOS: 78

<210> SEQ ID NO 1
<211> LENGTH: 105
<212> TYPE: PRT
<213> ORGANISM: Sus scrofa

<400> SEQUENCE: 1

His Arg Lys Pro Arg Leu Val Gly Gly Asp Ile Pro Cys Ser Gly Arg
1               5                   10                  15

Val Glu Val Gln His Gly Asp Thr Trp Gly Thr Val Cys Asp Ser Asp
            20                  25                  30

Phe Ser Leu Glu Ala Ala Ser Val Leu Cys Arg Glu Leu Gln Cys Gly
        35                  40                  45

Thr Val Val Ser Leu Leu Gly Gly Ala His Phe Gly Glu Gly Ser Gly
    50                  55                  60

Gln Ile Trp Ala Glu Glu Phe Gln Cys Glu Gly His Glu Ser His Leu
65                  70                  75                  80

Ser Leu Cys Pro Val Ala Pro Arg Pro Asp Gly Thr Cys Ser His Ser
                85                  90                  95

Arg Asp Val Gly Val Val Cys Ser Arg
            100                 105

<210> SEQ ID NO 2
<211> LENGTH: 6
<212> TYPE: DNA
<213> ORGANISM: Artificial Sequence
<220> FEATURE:
<223> OTHER INFORMATION: Insertion

<400> SEQUENCE: 2 ccgcgg                                                          6

<210> SEQ ID NO 3
<211> LENGTH: 29
<212> TYPE: DNA
<213> ORGANISM: Artificial Sequence
<220> FEATURE:
<223> OTHER INFORMATION: forward primer

<400> SEQUENCE: 3
attaccgcgg ccctgctctg gtcgtgttg                                29

<210> SEQ ID NO 4
<211> LENGTH: 30
<212> TYPE: DNA
<213> ORGANISM: Artificial Sequence
<220> FEATURE:
<223> OTHER INFORMATION: reverse primer

<400> SEQUENCE: 4
attaccgcgg aatgtcccct ccaaccagcc                               30

<210> SEQ ID NO 5
<211> LENGTH: 30
<212> TYPE: DNA
<213> ORGANISM: Artificial Sequence
<220> FEATURE:
<223> OTHER INFORMATION: forward primer

<400> SEQUENCE: 5
attaccgcgg tggggcaccg tctgtgattc                               30

<210> SEQ ID NO 6
<211> LENGTH: 34
<212> TYPE: DNA
<213> ORGANISM: Artificial Sequence
<220> FEATURE:
<223> OTHER INFORMATION: reverse primer

<400> SEQUENCE: 6
gtgaccgcgg cgtgtctcca tgttgtactt caac                          34

<210> SEQ ID NO 7
<211> LENGTH: 27
<212> TYPE: DNA
<213> ORGANISM: Artificial Sequence
<220> FEATURE:
<223> OTHER INFORMATION: forward primer

<400> SEQUENCE: 7
tataccgcgg ctggaggcgg ccagcgt                                  27

<210> SEQ ID NO 8
<211> LENGTH: 36
<212> TYPE: DNA
<213> ORGANISM: Artificial Sequence
<220> FEATURE:
<223> OTHER INFORMATION: reverse primer

<400> SEQUENCE: 8
cgctccgcgg agagaagtca gaatcacaga cggtgc                        36

<210> SEQ ID NO 9
<211> LENGTH: 34
<212> TYPE: DNA
<213> ORGANISM: Artificial Sequence
<220> FEATURE:
<223> OTHER INFORMATION: forward primer

<400> SEQUENCE: 9
atccccgcgg ctacagtgcg gcactgtggt ttcc                          34

<210> SEQ ID NO 10
<211> LENGTH: 31
<212> TYPE: DNA
<213> ORGANISM: Artificial Sequence
<220> FEATURE:
<223> OTHER INFORMATION: reverse primer

<400> SEQUENCE: 10
atcaccgcgg ttccctgcac agcacgctgg c                             31

<210> SEQ ID NO 11
<211> LENGTH: 42
<212> TYPE: DNA
<213> ORGANISM: Artificial Sequence
<220> FEATURE:
<223> OTHER INFORMATION: forward primer

<400> SEQUENCE: 11
caacccgcgg cactttggag aaggaagtgg acagatctgg gc                 42

<210> SEQ ID NO 12
<211> LENGTH: 34
<212> TYPE: DNA
<213> ORGANISM: Artificial Sequence
<220> FEATURE:
<223> OTHER INFORMATION: reverse primer

```
<400> SEQUENCE: 12
acacccgcgg agctccccc aggagggaaa ccac                              34

<210> SEQ ID NO 13
<211> LENGTH: 34
<212> TYPE: DNA
<213> ORGANISM: Artificial Sequence
<220> FEATURE:
<223> OTHER INFORMATION: forward primer

<400> SEQUENCE: 13
caccccgcgg gaattccagt gtgaggggca cgag                             34

<210> SEQ ID NO 14
<211> LENGTH: 34
<212> TYPE: DNA
<213> ORGANISM: Artificial Sequence
<220> FEATURE:
<223> OTHER INFORMATION: reverse primer

<400> SEQUENCE: 14 accccccgcgg ttcagcccag atctgtccac ttcc                            34

<210> SEQ ID NO 15
<211> LENGTH: 32
<212> TYPE: DNA
<213> ORGANISM: Artificial Sequence
<220> FEATURE:
<223> OTHER INFORMATION: forward primer

<400> SEQUENCE: 15
aaggccgcgg tcactctgcc cagtagcacc cc                               32

<210> SEQ ID NO 16
<211> LENGTH: 34
<212> TYPE: DNA
<213> ORGANISM: Artificial Sequence
<220> FEATURE:
<223> OTHER INFORMATION: reverse primer

<400> SEQUENCE: 16
cacaccgcgg aaggtgggac tcgtgcccct caca                             34

<210> SEQ ID NO 17
<211> LENGTH: 34
<212> TYPE: DNA
<213> ORGANISM: Artificial Sequence
<220> FEATURE:
<223> OTHER INFORMATION: forward primer

<400> SEQUENCE: 17
ccgaccgcgg acatgtagcc acagcaggga cgtc                             34

<210> SEQ ID NO 18
<211> LENGTH: 28
<212> TYPE: DNA
<213> ORGANISM: Artificial Sequence
<220> FEATURE:
<223> OTHER INFORMATION: reverse primer

<400> SEQUENCE: 18
tataccgcgg cccgtcaggg cggggtgc                                    28

<210> SEQ ID NO 19
```

```
<211> LENGTH: 34
<212> TYPE: DNA
<213> ORGANISM: Artificial Sequence
<220> FEATURE:
<223> OTHER INFORMATION: forward primer

<400> SEQUENCE: 19
cgcgccgcgg tgctcaagat acacacaaat ccgc                           34

<210> SEQ ID NO 20
<211> LENGTH: 30
<212> TYPE: DNA
<213> ORGANISM: Artificial Sequence
<220> FEATURE:
<223> OTHER INFORMATION: reverse primer

<400> SEQUENCE: 20
caacccgcgg gactacgccg acgtccctgc                                30

<210> SEQ ID NO 21
<211> LENGTH: 46
<212> TYPE: DNA
<213> ORGANISM: Artificial Sequence
<220> FEATURE:
<223> OTHER INFORMATION: Forward primer

<400> SEQUENCE: 21
cacaccgcgg cttttgttgc acttgcaatc tttggggtca ttctgt              46

<210> SEQ ID NO 22
<211> LENGTH: 39
<212> TYPE: DNA
<213> ORGANISM: Artificial Sequence
<220> FEATURE:
<223> OTHER INFORMATION: Reverse primer

<400> SEQUENCE: 22
cccaccgcgg ctgtggcatg tagggattct cggctctttt                     39

<210> SEQ ID NO 23
<211> LENGTH: 42
<212> TYPE: DNA
<213> ORGANISM: Artificial Sequence
<220> FEATURE:
<223> OTHER INFORMATION: Forward primer

<400> SEQUENCE: 23
cacaccgcgg gtcgctcatc ttttgttgca cttgcaatct tt                  42

<210> SEQ ID NO 24
<211> LENGTH: 34
<212> TYPE: DNA
<213> ORGANISM: Artificial Sequence
<220> FEATURE:
<223> OTHER INFORMATION: Reverse primer

<400> SEQUENCE: 24
aacaccgcgg ctgagcacgt cacagcagca tcct                           34

<210> SEQ ID NO 25
<211> LENGTH: 27
<212> TYPE: DNA
<213> ORGANISM: Artificial Sequence
<220> FEATURE:
<223> OTHER INFORMATION: Forward primer

<400> SEQUENCE: 25
```

```
ggtaccggat ctgatttaga gatgagg                                          27

<210> SEQ ID NO 26
<211> LENGTH: 27
<212> TYPE: DNA
<213> ORGANISM: Artificial Sequence
<220> FEATURE:
<223> OTHER INFORMATION: Reverse primer

<400> SEQUENCE: 26
tctagattgt acttcagagt ggtctcc                                          27

<210> SEQ ID NO 27
<211> LENGTH: 24
<212> TYPE: DNA
<213> ORGANISM: Artificial Sequence
<220> FEATURE:
<223> OTHER INFORMATION: Forward primer

<400> SEQUENCE: 27
ggtaccggag cagacctgaa actg                                             24

<210> SEQ ID NO 28
<211> LENGTH: 22
<212> TYPE: DNA
<213> ORGANISM: Artificial Sequence
<220> FEATURE:
<223> OTHER INFORMATION: Forward primer

<400> SEQUENCE: 28
ggtacccaca ggaaacccag gc                                               22

<210> SEQ ID NO 29
<211> LENGTH: 21
<212> TYPE: DNA
<213> ORGANISM: Artificial Sequence
<220> FEATURE:
<223> OTHER INFORMATION: Forward primer

<400> SEQUENCE: 29
ggtacctaca cacaaatccg c                                                21

<210> SEQ ID NO 30
<211> LENGTH: 24
<212> TYPE: DNA
<213> ORGANISM: Artificial Sequence
<220> FEATURE:
<223> OTHER INFORMATION: Forward primer

<400> SEQUENCE: 30
ggtaccagtg gtcaacttcg cctg                                             24

<210> SEQ ID NO 31
<211> LENGTH: 33
<212> TYPE: DNA
<213> ORGANISM: Artificial Sequence
<220> FEATURE:
<223> OTHER INFORMATION: Forward primer

<400> SEQUENCE: 31
ggtaccaaaa taagacttca agaaggaaac act                                   33

<210> SEQ ID NO 32
<211> LENGTH: 24
<212> TYPE: DNA
```

```
<213> ORGANISM: Artificial Sequence
<220> FEATURE:
<223> OTHER INFORMATION: Forward primer

<400> SEQUENCE: 32
ggtaccatgt acacacaaat ccgc                                              24

<210> SEQ ID NO 33
<211> LENGTH: 24
<212> TYPE: DNA
<213> ORGANISM: Artificial Sequence
<220> FEATURE:
<223> OTHER INFORMATION: Reverse primer

<400> SEQUENCE: 33
tctagattct gagcacgtca cagc                                              24

<210> SEQ ID NO 34
<211> LENGTH: 39
<212> TYPE: DNA
<213> ORGANISM: Artificial Sequence
<220> FEATURE:
<223> OTHER INFORMATION: Forward primer

<400> SEQUENCE: 34
attattaatt aagtttgttg cacttgcaat ctttggggt                              39

<210> SEQ ID NO 35
<211> LENGTH: 41
<212> TYPE: DNA
<213> ORGANISM: Artificial Sequence
<220> FEATURE:
<223> OTHER INFORMATION: Reverse primer

<400> SEQUENCE: 35
atcattaatt aaatttaagc aaatcactcc agcatcctca g                           41

<210> SEQ ID NO 36
<211> LENGTH: 31
<212> TYPE: DNA
<213> ORGANISM: Artificial Sequence
<220> FEATURE:
<223> OTHER INFORMATION: Reverse sequence

<400> SEQUENCE: 36
atcgttaatt aatcttgagc agactacgcc g                                      31

<210> SEQ ID NO 37
<211> LENGTH: 33
<212> TYPE: DNA
<213> ORGANISM: Artificial Sequence
<220> FEATURE:
<223> OTHER INFORMATION: Reverse primer

<400> SEQUENCE: 37
cagtttaatt aactctgagc agatgactcc tgc                                    33

<210> SEQ ID NO 38
<211> LENGTH: 38
<212> TYPE: DNA
<213> ORGANISM: Artificial Sequence
<220> FEATURE:
<223> OTHER INFORMATION: Forward primer

<400> SEQUENCE: 38
cactttaatt aagtacacac aaatccgctt ggtgaatg                               38
```

<210> SEQ ID NO 39
<211> LENGTH: 36
<212> TYPE: DNA
<213> ORGANISM: Artificial Sequence
<220> FEATURE:
<223> OTHER INFORMATION: Reverse primer

<400> SEQUENCE: 39
catattaatt aaggctgagc aggtaatttt ggcttc                              36

<210> SEQ ID NO 40
<211> LENGTH: 41
<212> TYPE: DNA
<213> ORGANISM: Artificial Sequence
<220> FEATURE:
<223> OTHER INFORMATION: Forward primer

<400> SEQUENCE: 40
attattaatt aagattgcaa agagccgaga atccctacat g                        41

<210> SEQ ID NO 41
<211> LENGTH: 41
<212> TYPE: DNA
<213> ORGANISM: Artificial Sequence
<220> FEATURE:
<223> OTHER INFORMATION: Reverse primer

<400> SEQUENCE: 41
atcattaatt aaatttaagc aaatcactcc agcatcctca g                        41

<210> SEQ ID NO 42
<211> LENGTH: 31
<212> TYPE: DNA
<213> ORGANISM: Artificial Sequence
<220> FEATURE:
<223> OTHER INFORMATION: Reverse primer

<400> SEQUENCE: 42
atcgttaatt aatcttgagc agactacgcc g                                   31

<210> SEQ ID NO 43
<211> LENGTH: 36
<212> TYPE: DNA
<213> ORGANISM: Artificial Sequence
<220> FEATURE:
<223> OTHER INFORMATION: Forward primer

<400> SEQUENCE: 43
caccccgcgg gaagtacaac atggagacac gtgggg                              36

<210> SEQ ID NO 44
<211> LENGTH: 34
<212> TYPE: DNA
<213> ORGANISM: Artificial Sequence
<220> FEATURE:
<223> OTHER INFORMATION: Reverse primer

<400> SEQUENCE: 44
accaccgcgg aacacgacca gagcagggaa tgtc                                34

<210> SEQ ID NO 45
<211> LENGTH: 37
<212> TYPE: DNA
<213> ORGANISM: Artificial Sequence
<220> FEATURE:

<223> OTHER INFORMATION: Forward primer

<400> SEQUENCE: 45
gataccgcgg ctgtgcaggg aactacagtg cggcact        37

<210> SEQ ID NO 46
<211> LENGTH: 34
<212> TYPE: DNA
<213> ORGANISM: Artificial Sequence
<220> FEATURE:
<223> OTHER INFORMATION: Reverse primer

<400> SEQUENCE: 46
tataccgcgg cacgctggcc gcctccagag agaa           34

<210> SEQ ID NO 47
<211> LENGTH: 28
<212> TYPE: DNA
<213> ORGANISM: Artificial Sequence
<220> FEATURE:
<223> OTHER INFORMATION: Forward primer

<400> SEQUENCE: 47
cacaccgcgg tgcggcactg tggtttcc                  28

<210> SEQ ID NO 48
<211> LENGTH: 32
<212> TYPE: DNA
<213> ORGANISM: Artificial Sequence
<220> FEATURE:
<223> OTHER INFORMATION: Reverse primer

<400> SEQUENCE: 48
taacccgcgg ctgtagttcc ctgcacagca cg             32

<210> SEQ ID NO 49
<211> LENGTH: 24
<212> TYPE: DNA
<213> ORGANISM: Artificial Sequence
<220> FEATURE:
<223> OTHER INFORMATION: Forward primer

<400> SEQUENCE: 49
cacaccgcgg gtttccctcc tggg                      24

<210> SEQ ID NO 50
<211> LENGTH: 28
<212> TYPE: DNA
<213> ORGANISM: Artificial Sequence
<220> FEATURE:
<223> OTHER INFORMATION: Reverse primer

<400> SEQUENCE: 50
cccaccgcgg cacagtgccg cactgtag                  28

<210> SEQ ID NO 51
<211> LENGTH: 39
<212> TYPE: DNA
<213> ORGANISM: Artificial Sequence
<220> FEATURE:
<223> OTHER INFORMATION: Forward primer

<400> SEQUENCE: 51
caacccgcgg gaaggaagtg gacagatctg ggctgaaga      39

<210> SEQ ID NO 52
<211> LENGTH: 33
<212> TYPE: DNA
<213> ORGANISM: Artificial Sequence
<220> FEATURE:
<223> OTHER INFORMATION: Reverse primer

<400> SEQUENCE: 52
attaccgcgg tccaaagtga gctcccccca gga                                33

<210> SEQ ID NO 53
<211> LENGTH: 37
<212> TYPE: DNA
<213> ORGANISM: Artificial Sequence
<220> FEATURE:
<223> OTHER INFORMATION: Forward primer

<400> SEQUENCE: 53
caacccgcgg cagatctggg ctgaagaatt ccagtgt                            37

<210> SEQ ID NO 54
<211> LENGTH: 38
<212> TYPE: DNA
<213> ORGANISM: Artificial Sequence
<220> FEATURE:
<223> OTHER INFORMATION: Reverse primer

<400> SEQUENCE: 54
cacaccgcgg tccacttcct tctccaaagt gagctccc                           38

<210> SEQ ID NO 55
<211> LENGTH: 4
<212> TYPE: PRT
<213> ORGANISM: Sus scrofa

<400> SEQUENCE: 55

Gly Arg Ser Ser
1

<210> SEQ ID NO 56
<211> LENGTH: 6
<212> TYPE: DNA
<213> ORGANISM: Artificial Sequence
<220> FEATURE:
<223> OTHER INFORMATION: SacII restriction site

<400> SEQUENCE: 56 ccgcgg                                                              6

<210> SEQ ID NO 57
<211> LENGTH: 16
<212> TYPE: PRT
<213> ORGANISM: Sus scrofa

<400> SEQUENCE: 57

Glu Ile Ala Lys Ser Arg Glu Ser Leu His Ala Thr Gly Arg Ser Ser
1               5                   10                  15

<210> SEQ ID NO 58
<211> LENGTH: 104
<212> TYPE: PRT
<213> ORGANISM: Sus scrofa

<400> SEQUENCE: 58

Ala His Arg Lys Pro Arg Leu Val Gly Asp Ile Pro Cys Ser Gly Arg
1               5                   10                  15

```
Val Glu Val Gln His Gly Asp Thr Trp Gly Thr Val Cys Asp Ser Asp
         20                  25                  30

Phe Ser Leu Glu Ala Ala Ser Val Leu Cys Arg Glu Leu Gln Cys Gly
             35                  40                  45

Thr Val Val Ser Leu Leu Gly Gly Ala His Phe Gly Glu Gly Ser Gly
 50                  55                  60

Gln Ile Trp Ala Glu Glu Phe Gln Cys Glu Gly His Glu Ser His Leu
65                  70                  75                  80

Ser Leu Cys Pro Val Ala Pro Arg Pro Asp Gly Thr Cys Ser His Ser
                 85                  90                  95

Arg Asp Val Gly Val Val Cys Ser
            100

<210> SEQ ID NO 59
<211> LENGTH: 6
<212> TYPE: DNA
<213> ORGANISM: Artificial Sequence
<220> FEATURE:
<223> OTHER INFORMATION: Sac II restriction site

<400> SEQUENCE: 59 ccccgg                                                                  6

<210> SEQ ID NO 60
<211> LENGTH: 100
<212> TYPE: PRT
<213> ORGANISM: Sus scrofa

<400> SEQUENCE: 60

Pro Arg Leu Val Gly Asp Ile Pro Cys Ser Gly Arg Val Glu Val Gln
1               5                   10                  15

His Gly Asp Thr Trp Gly Thr Val Cys Asp Ser Asp Phe Ser Leu Glu
             20                  25                  30

Ala Ala Ser Val Leu Cys Arg Glu Leu Gln Cys Gly Thr Val Val Ser
         35                  40                  45

Leu Leu Gly Gly Ala His Phe Gly Glu Gly Ser Gly Gln Ile Trp Ala
 50                  55                  60

Glu Glu Phe Gln Cys Glu Gly His Glu Ser His Leu Ser Leu Cys Pro
65                  70                  75                  80

Val Ala Pro Arg Pro Asp Gly Thr Cys Ser His Ser Arg Asp Val Gly
                 85                  90                  95

Val Val Cys Ser
            100

<210> SEQ ID NO 61
<211> LENGTH: 5
<212> TYPE: PRT
<213> ORGANISM: Sus scrofa

<400> SEQUENCE: 61

Ala Val Thr Cys Ser
1               5

<210> SEQ ID NO 62
<211> LENGTH: 5
<212> TYPE: PRT
<213> ORGANISM: Sus scrofa

<400> SEQUENCE: 62
```

```
Phe Val Ala Leu Ala
1               5

<210> SEQ ID NO 63
<211> LENGTH: 5
<212> TYPE: PRT
<213> ORGANISM: Sus scrofa

<400> SEQUENCE: 63

Lys Ile Thr Cys Ser
1               5

<210> SEQ ID NO 64
<211> LENGTH: 4
<212> TYPE: PRT
<213> ORGANISM: Sus scrofa

<400> SEQUENCE: 64

Ala His Arg Lys
1

<210> SEQ ID NO 65
<211> LENGTH: 4
<212> TYPE: PRT
<213> ORGANISM: Artificial Sequence
<220> FEATURE:
<223> OTHER INFORMATION: Modified construct for the interdomain sequence

<400> SEQUENCE: 65

Ala Ala Ala Ala
1

<210> SEQ ID NO 66
<211> LENGTH: 4
<212> TYPE: PRT
<213> ORGANISM: Artificial Sequence
<220> FEATURE:
<223> OTHER INFORMATION: Modified construct for the interdomain sequence

<400> SEQUENCE: 66

Ala Ala Ala Lys
1

<210> SEQ ID NO 67
<211> LENGTH: 4
<212> TYPE: PRT
<213> ORGANISM: Artificial Sequence
<220> FEATURE:
<223> OTHER INFORMATION: Modified construct for the interdomain sequence

<400> SEQUENCE: 67

Ala His Ala Ala
1

<210> SEQ ID NO 68
<211> LENGTH: 4
<212> TYPE: PRT
<213> ORGANISM: Artificial Sequence
<220> FEATURE:
<223> OTHER INFORMATION: Modified construct for the interdomain sequence

<400> SEQUENCE: 68

Ala Ala Arg Ala
1

<210> SEQ ID NO 69
```

```
<211> LENGTH: 4
<212> TYPE: PRT
<213> ORGANISM: Artificial Sequence
<220> FEATURE:
<223> OTHER INFORMATION: Modified construct for the interdomain sequence

<400> SEQUENCE: 69

Ala Ala Arg Lys
1

<210> SEQ ID NO 70
<211> LENGTH: 4
<212> TYPE: PRT
<213> ORGANISM: Artificial Sequence
<220> FEATURE:
<223> OTHER INFORMATION: Modified construct for the interdomain sequence

<400> SEQUENCE: 70

Ala His Arg Arg
1

<210> SEQ ID NO 71
<211> LENGTH: 4
<212> TYPE: PRT
<213> ORGANISM: Artificial Sequence
<220> FEATURE:
<223> OTHER INFORMATION: Modified construct for the interdomain sequence

<400> SEQUENCE: 71

Ala His Lys Arg
1

<210> SEQ ID NO 72
<211> LENGTH: 4
<212> TYPE: PRT
<213> ORGANISM: Artificial Sequence
<220> FEATURE:
<223> OTHER INFORMATION: Modified construct for the interdomain sequence

<400> SEQUENCE: 72

Ala Lys Lys Lys
1

<210> SEQ ID NO 73
<211> LENGTH: 4
<212> TYPE: PRT
<213> ORGANISM: Artificial Sequence
<220> FEATURE:
<223> OTHER INFORMATION: Modified construct for the interdomain sequence

<400> SEQUENCE: 73

Asp His Arg Lys
1

<210> SEQ ID NO 74
<211> LENGTH: 5
<212> TYPE: PRT
<213> ORGANISM: Artificial Sequence
<220> FEATURE:
<223> OTHER INFORMATION: Modified construct for the interdomain sequence

<400> SEQUENCE: 74

Ala His Arg Ala Lys
1               5

<210> SEQ ID NO 75
<211> LENGTH: 5
```

```
<212> TYPE: PRT
<213> ORGANISM: Artificial Sequence
<220> FEATURE:
<223> OTHER INFORMATION: Modified construct for the interdomain sequence

<400> SEQUENCE: 75

Ala His Ala Arg Lys
1               5

<210> SEQ ID NO 76
<211> LENGTH: 5
<212> TYPE: PRT
<213> ORGANISM: Sus scrofa

<400> SEQUENCE: 76

Pro Arg Leu Val Gly
1               5

<210> SEQ ID NO 77
<211> LENGTH: 25
<212> TYPE: PRT
<213> ORGANISM: Artificial Sequence
<220> FEATURE:
<223> OTHER INFORMATION: Modified construct for the PST II domain
      sequence

<400> SEQUENCE: 77

Ala Val Thr Cys Ser Glu Ile Ala Lys Ser Arg Glu Ser Leu His Ala
1               5                   10                  15

Ala Ala Ala Ser Phe Val Ala Leu Ala
            20                  25

<210> SEQ ID NO 78
<211> LENGTH: 16
<212> TYPE: PRT
<213> ORGANISM: Artificial Sequence
<220> FEATURE:
<223> OTHER INFORMATION: Modified construct for the PST II domain
      sequence

<400> SEQUENCE: 78

Ala Val Thr Cys Ser Ala Ala Gly Arg Ser Ser Phe Val Ala Leu Ala
1               5                   10                  15
```